United States Patent
Marquess et al.

(10) Patent No.: US 8,044,045 B2
(45) Date of Patent: Oct. 25, 2011

(54) INDAZOLE-CARBOXAMIDE COMPOUNDS AS 5-HT$_4$ RECEPTOR AGONISTS

(75) Inventors: Daniel Marquess, Half Moon Bay, CA (US); Seok-Ki Choi, Ann Arbor, MI (US); Paul R. Fatheree, San Francisco, CA (US); Roland Gendron, San Francisco, CA (US); Adam A. Goldblum, Berkeley, CA (US); Daniel D. Long, San Francisco, CA (US); S. Derek Turner, Reston, VA (US); Jyanwei Liu, Sunnyvale, CA (US)

(73) Assignee: Theravance, Inc., South San Francisco, CA (US)

(*) Notice: Subject to any disclaimer, the term of this patent is extended or adjusted under 35 U.S.C. 154(b) by 0 days.

(21) Appl. No.: 12/689,763

(22) Filed: Jan. 19, 2010

(65) Prior Publication Data

US 2010/0261716 A1     Oct. 14, 2010

Related U.S. Application Data

(60) Continuation of application No. 12/012,579, filed on Feb. 4, 2008, now Pat. No. 7,674,908, which is a division of application No. 11/060,195, filed on Feb. 17, 2005, now Pat. No. 7,351,704.

(60) Provisional application No. 60/545,702, filed on Feb. 18, 2004.

(51) Int. Cl.
*A61K 31/541* (2006.01)
*A61K 31/496* (2006.01)
*A61K 31/46* (2006.01)
*A61P 1/00* (2006.01)

(52) U.S. Cl. ............ 514/228.2; 514/253.04; 514/304

(58) Field of Classification Search ............ 514/228.2, 514/253.04, 304
See application file for complete search history.

(56) References Cited

U.S. PATENT DOCUMENTS

| | | | |
|---|---|---|---|
| 4,321,378 A * | 3/1982 | Dostert et al. | |
| 4,845,092 A * | 7/1989 | Sanger et al. | |
| 4,853,394 A * | 8/1989 | King et al. | |
| 4,937,247 A * | 6/1990 | King | |
| 5,017,573 A * | 5/1991 | Kon et al. | |
| 5,037,844 A * | 8/1991 | Hamminga et al. | |
| 5,047,410 A * | 9/1991 | Donetti et al. | |
| 5,223,511 A * | 6/1993 | Turconi et al. | |
| 5,248,684 A * | 9/1993 | Suzuki et al. | |
| 5,272,154 A * | 12/1993 | Dixon et al. | |
| 5,298,510 A * | 3/1994 | Tyers | |
| 5,319,085 A * | 6/1994 | Suzuki et al. | |
| 5,552,398 A * | 9/1996 | King et al. | |
| 5,561,149 A * | 10/1996 | Azria et al. | |
| 5,571,820 A * | 11/1996 | Ohuchi et al. | |
| 5,654,320 A * | 8/1997 | Catlow et al. | |
| 5,684,003 A * | 11/1997 | Kikuchi et al. | |
| 5,696,129 A * | 12/1997 | King et al. | |
| 5,733,917 A * | 3/1998 | Ohuchi et al. | |
| 5,741,801 A * | 4/1998 | King et al. | |
| 5,753,673 A * | 5/1998 | Ohuchi et al. | |
| 5,773,436 A * | 6/1998 | Muller et al. | |
| 5,864,039 A * | 1/1999 | Kawakita et al. | |
| 5,914,405 A * | 6/1999 | Wilson | |
| 5,945,434 A * | 8/1999 | Suzuki et al. | |
| 6,002,009 A * | 12/1999 | Cereda et al. | |
| 6,117,882 A * | 9/2000 | Schaus et al. | |
| 6,172,062 B1 * | 1/2001 | Clark et al. | |
| 6,197,769 B1 * | 3/2001 | Alisi et al. | |
| 6,281,218 B1 * | 8/2001 | Cereda et al. | |
| 6,294,555 B1 * | 9/2001 | Kato et al. | |
| 6,452,013 B1 * | 9/2002 | Bosmans et al. | |
| 6,544,997 B1 * | 4/2003 | Bosmans et al. | |
| 6,624,162 B2 * | 9/2003 | Uchida et al. | |
| 6,696,468 B2 * | 2/2004 | Kato et al. | |
| 7,351,704 B2 * | 4/2008 | Marquess et al. | |
| 2002/0173505 A1 * | 11/2002 | Skogvall | |
| 2003/0207875 A1 * | 11/2003 | Gymer et al. | |
| 2004/0122043 A1 * | 6/2004 | Iguchi et al. | |
| 2004/0127514 A1 * | 7/2004 | Katsu et al. | |
| 2004/0266814 A1 * | 12/2004 | Noguchi et al. | |
| 2005/0148573 A1 | 7/2005 | Katsu et al. | |

FOREIGN PATENT DOCUMENTS

| | | | |
|---|---|---|---|
| EP | 0 309 423 A2 | 3/1989 | |
| EP | 0 623 621 A1 | 11/1994 | |
| ES | 2 154 605 A1 | 4/2001 | |
| IT | 01298271 B1 | 12/1999 | |
| JP | 04005289 A2 | 1/1992 | |
| JP | 08231544 A2 | 9/1996 | |
| WO | WO 93/03725 A1 | 3/1993 | |
| WO | WO 97/35860 A1 | 10/1997 | |
| WO | WO 99/20633 A1 | 4/1999 | |
| WO | WO 00/63215 A2 | 10/2000 | |
| WO | WO 01/25236 A2 | 4/2001 | |
| WO | WO 02/36113 A1 | 5/2002 | |
| WO | WO 2005/000837 A1 | 1/2005 | |
| WO | WO 2005/000838 A1 | 1/2005 | |
| WO | WO 2005/021539 A1 | 3/2005 | |
| WO | WO 2004/026868 A1 | 4/2005 | |
| WO | WO 2005/049608 A1 | 6/2005 | |
| WO | WO 2005/073222 A1 | 8/2005 | |

OTHER PUBLICATIONS

Kim et al., Neurogastroenterology and motility : the official journal of the European Gastrointestinal Motility Society, (Feb. 2008) vol. 20, No. 2, pp. 169-176.*
U.S. Appl. No. 12/842,389, Fatheree et al.*
Allegretti et al., "One-pot, new stereoselective synthesis of endo-tropanamine", Tetrahedron Letters 42, pp. 4257-4259 (2001).

(Continued)

Primary Examiner — D M Seaman
Assistant Examiner — Niloofar Rahmani
(74) Attorney, Agent, or Firm — Jeffrey A. Hagenah; Roberta P. Saxon

(57) ABSTRACT

The invention provides novel indazole-carboxamide 5-HT$_4$ receptor agonist compounds. The invention also provides pharmaceutical compositions comprising such compounds, methods of using such compounds to treat diseases associated with 5-HT$_4$ receptor activity, and processes and intermediates useful for preparing such compounds.

10 Claims, No Drawings

OTHER PUBLICATIONS

Baxter et al., "Benzimidazolone derivatives act as 5-HT$_4$ receptor ligands in rat oesophagus", European Journal of Pharmacology, 212, pp. 225-229 (1992).

Berdini et al., "A modified palladium catalysed reductive amination procedure", Tetrahedron 58, pp. 5669-5674 (2002).

Bermudez et al., "5-Hydroxytryptamine (5-HT$_3$) Receptor Antagonists. 1. Indazole and Indolizine-3-carboxylic Acid Derivatives", J. Med. Chem., 33, pp. 1924-1929 (1990).

Blum et al., "Design and Synthesis of Novel Ligands for the 5-HT$_3$ and the 5-HT$_4$ Receptor", Bioorganic & Medicinal Chemistry Letters, vol. 2, No. 5, pp. 461-466 (1992).

Curtet et al., "New Arylpiperazine Derivatives as Antagonists of the Human Cloned 5-HT$_4$ Receptor Isoforms", J. Med. Chem., 43, pp. 3761-3769 (2000).

Dumuis et al., "Characterization of a novel 5-HT$_4$ receptor antagonist of the azabicycloalkyl benzimidazolone class: DAU 6285", Naunyn-Schmiedeberg's Arch Pharmacol, 345, pp. 264-269 (1992).

Dumuis et al., "Azabicycloalkyl benzimidazolone derivatives as a novel class of potent agonists at the 5-HT$_4$ receptor positively coupled to adenylate cyclase in brain", Naunyn-Schmiedeberg's Arch Pharmacol, 343, pp. 245-251 (1991).

Fake et al., "BRL 43694: A Potent and Novel 5-HT$_3$ Receptor Antagonist", Br. J. Pharmacol., 91, 335P (1987).

Kaumann et al., "Indazole as an Indole Bioisostere:5-HT$_4$ Receptor Antagonism.", Bioorganic & Medicinal Chemistry Letters, vol. 2, No. 5, pp. 419-420 (1992).

Langlois et al., "5-HT$_4$ Receptor Ligands: Applications and New Prospects", J. Med Chem, vol. 46, No. 3, pp. 319-344 (2003).

Lopez-Rodriguez et al., "3-D-QSAR/CoMFA and Recognition Models of Benzimidazole Derivatives at the 5-HT$_4$ Receptor", Bioorganic & Medicinal Chemistry Letters, 11, pp. 2807-2811 (2001).

Lopez-Rodriguez et al., "Benzimidazole Derivates. Part 1: Synthesis and Structure-Activity Relationships of New Benzimidazole-4-carboxamides and Carboxylates as Potent and Selective 5-HT$_4$ Receptor Antagonists", Bioorganic & Medicinal Chemistry, 7, pp. 2271-2281 (1999).

Lopez-Rodriguez et al., "Benzimidazole Derivatives. 3. 3D-QSAR/CoMFA Model and Computational Simulation for the Recognition of 5-HT$_4$ Receptor Antagonists", J. Med. Chem., 45, pp. 4806-4815 (2002).

Lopez-Rodriguez et al., "Benzimidazone derivatives 4. The recognition of the voluminous substituent attached to the basic amino group of 5-HT$_4$ receptor antagonists", Journal of Computer-Aided Molecular Design, 17, pp. 515-524 (2003).

Lopez-Rodriguez et al., "Design and Synthesis of New Benzimidazole-Arylpiperazine Derivatives Acting as Mixed 5-HT$_{1A}$/5-HT$_3$ Ligands", Bioorganic & Medicinal Chemistry Letters, 13, pp. 3177-3180 (2003).

Lopez-Rodriguez et al., "Study of the bioactive conformation of novel 5-HT$_4$ receptor ligands: influence of an intramolecular hydrogen bond", Tetrahedron, 57, pp. 6745-6749 (2001).

Schaus et al., "Synthesis and Structure-Activity Relationships of Potent and Orally Active 5-HT$_4$ Receptor Antagonists: Indazole and Benzimidazolone Derivatives", J. Med. Chem., 41, pp. 1943-1955 (1998).

Suzuki et al., "Synthesis and Evaluation of Novel 2-Oxo-1,2-dihydro-3-quinolinecarboxamide Derivatives as Potent and Selective Serotonin 5-HT$_4$ Receptor Agonists", Chem. Pharm. Bull., 49(1), pp. 29-39 (2001).

Suzuki et al., "A Practical Procedure for Preparation of N-(endo-8-3-hydroxy)propyl-8-azabicyclo[3.2.1]oct-3-yl)-1-isopropyl-2-oxo-1,2-dihydro-3-quinoline-carboxamide (TS-951)", Heterocycles, vol. 53, No. 11, pp. 2471-2485 (2000).

Suzuki et al., "Synthesis and Evaluation of Novel 2-Oxo-1,2-dihydro-3-quinolinecarboxamide Derivatives as Serotonin 5-HT$_4$ Receptor Agonists", Chem. Pharm. Bull., 48(12), pp. 2003-2008 (2000).

Tapia et al., "2,3-Dihydro-2-oxo-1H-benzimidazole-1-carboxamides with Selective Affinity for the 5-HT$_4$ Receptor: Synthesis and Structure-Affinity and Structure-Activity Relationships of a New Series of Partial Agonist and Antagonist Derivatives", J. Med. Chem., 42, pp. 2870-2880 (1999).

Turconi et al., "Azabicycloalkyl benzimidazolones: Interaction with serotonergic 5-HT$_3$ and 5-HT$_4$ receptors and potential therapeutic implications", Drugs of the Future, 16(11), pp. 1011-1026 (1991).

Turconi et al., "Synthesis of a New Class of 2,3-Dihydro-2-oxo-1H-benzimidazole-1-carobxylic Acid Derivatives as Highly Potent 5-HT$_3$ Receptor Antagonists", J. Med. Chem., 33, pp. 2101-2108 (1990).

Abstract of JP 04089489 A2, "Preparation of azabicyclo compound quaternary ammonium salts as 5-HT3 receptor antagonists", published Mar. 23, 1992, Chemical Abstracts Accession No. CAN 117:19164.

Abstract of JP 07324087 A2, "Preparation of 2-oxo-1,2-dihydro-4-quinolinecarboxylic acid derivatives as serotonin receptor stimulants", published Dec. 12, 1995, Chemical Abstracts Accession No. CAN 124:260866.

Abstract of JP 08034783 A2, "Preparation of N-(8-azabicyclo[3.2.1]oct-3-yl)-2-oxo,1,2-dihydro-3-quinolinecarboxamide and (8-azabicyclo[3.2.1]oct-3-yl)-2-oxo,1,2-dihydro-3-quinoline-carboxylate derivatives as stimulants of serotonin (5-HT4) receptor", published Feb. 6, 1996, Chemical Abstracts Accession No. CAN 124:343137.

Abstract of JP 08034785 A2, "Preparation of N-(8-azoniabicyclo[3.2.1]oct-3-yl)-2-oxo,1,2-dihydro-3-quinolinecarboxamide and (8-azoniabicyclo[3.2.1]oct-3-yl)-2-oxo,1,2-dihydro-3-quinolinecarboxylate derivatives as stimulants of serotonin 4 (5-HT4) receptor", published Feb. 6, 1996, Chemical Abstracts Accession No. CAN 124:343138.

Abstract of JP 09194374 A2, "Digestive tract disease-treating agents", published Jul. 29, 1997, Chemical Abstracts Accession No. CAN 127:210377.

Abstract of JP 09241241 A2, "Preparation of N-(1-substituted-4-piperidyl)benzamides having serotonin receptor agonist activity", published Sep. 16, 1997, Chemical Abstracts Accession No. CAN 127:293254.

Abstract of JP 11001472 A2, "Preparation of 4-amino-5-halo-2-alkoxy-N-(4-piperidinylalkyl or 4-piperidinyl carbonyl)benzamides for improving digestive tract function", published Jan. 6, 1999, Chemical Abstracts Accession No. CAN 130:139257.

Abstract of JP 2001122784 A2, "Pharmaceuticals containing 1-[(1-substituted 4-piperidinyl)methyl]-4-piperidines as serotonin 4 receptor agonists", published May 8, 2001, Chemical Abstracts Accession No. CAN 134:348274.

Abstract of JP 2004277318 A2, "1-(1-Substitued-4-piperidinylmethyl)piperidine derivatives as 5-HT4 receptor agonists, pharmaceutical compositions containing them, and their use", published Oct. 7, 2004, Chemical Abstracts Accession No. CAN 141:307555.

Abstract of JP 2004277319 A2, "1-(4-piperidinylmethyl)piperidinylamide derivatives as 5-HT4 receptor agonists, pharmaceutical compositions containing them, and their use", published Oct. 7, 2004, Chemical Abstracts Accession No. CAN 141:307556.

Abstract of JP 2004277320 A2, "1,4-disubstituted piperidine derivatives as 5-HT4 receptor agonists, pharmaceutical compositions containing them, and their use", published Oct. 7, 2004, Chemical Abstracts Accession No. CAN 141:307557.

Harada et al., "Novel N-[1-(1-Substituted 4-Piperidinylmethyl)-4-piperidinyl]benzamides as Potent Colonic Prokinetic Agents", Bioorganic & Medicinal Chemistry Letters 12, pp. 967-970 (2002).

Bouras et al., "Prucalopride Accelerates Gastrointestinal and Colonic Transit in Patients with Constipation without a Rectal Evacuation Disorder", Gastroenterology, 120, pp. 354-360 (2001).

Briejer et al., "The in vitro pharmacological profile of prucalopride, a novel enterokinetic compound", European Journal of Pharmacology, 423, pp. 71-83 (2001).

Briejer et al., "Effects of the enterokinetic prucalopride (R093877) on colonic motility in fasted dogs", Neurogastroenterol. Mot., 13, pp. 465-472 (2001).

De Winter et al., "Effect of different prokinetic agents and a novel enterokinetic agent on postoperative ileus in rats", Gut, 45, pp. 713-718 (1999).

Grider et al., "5-Hydroxytryptamine4 receptor agonists initiate the peristaltic reflex in human, rat, and guinea pig intestine", Gastroenterology, 115, pp. 370-380 (1998).

Gullikson et al., "SC-49518 enhances gastric emptying of solid and liquid meals and stimulates gastrointestinal motility in dogs by a 5-hydroxytryptamine4 receptor mechanism", The Journal of Pharmacology and Experimental Therapeutics, 264(1), pp. 240-248 (1992).

Muller-Lissner et al., "Tegaserod is effective in the initial and retreatment of irritable bowel syndrome with constipation", Aliment Pharmacol Ther, 21, pp. 11-20 (2005).

Zelnorm®, Physicians Desk Reference, PDR® Electronic Library (TM), http://www.thomsonhc.com/pdrel/librarian/ND_PR/Pdr/PFPUI/a31qVUv1Lt1cXv/DDAK/ ... Mar. 6, 2007.

* cited by examiner

INDAZOLE-CARBOXAMIDE COMPOUNDS AS 5-HT$_4$ RECEPTOR AGONISTS

CROSS-REFERENCE TO RELATED APPLICATIONS

This application is a continuation of U.S. application Ser. No. 12/012,579, filed Feb. 4, 2008; now U.S. Pat. No. 7,674,908 B2, which is a divisional of U.S. application Ser. No. 11/060,195, filed Feb. 17, 2005, now U.S. Pat. No. 7,351,704, B2, which claims the benefit of U.S. Provisional Application No. 60/545,702, filed on Feb. 18, 2004; the entire disclosures of which are incorporated herein by reference in their entirety.

BACKGROUND OF THE INVENTION

1. Field of the Invention

The invention is directed to indazole-carboxamide compounds which are useful as 5-HT$_4$ receptor agonists. The invention is also directed to pharmaceutical compositions comprising such compounds, methods of using such compounds for treating medical conditions mediated by 5-HT$_4$ receptor activity, and processes and intermediates useful for preparing such compounds.

2. State of the Art

Serotonin (5-hydroxytryptamine, 5-HT) is a neurotransmitter that is widely distributed throughout the body, both in the central nervous system and in peripheral systems. At least seven subtypes of serotonin receptors have been identified and the interaction of serotonin with these different receptors is linked to a wide variety of physiological functions. There has been, therefore, substantial interest in developing therapeutic agents that target specific 5-HT receptor subtypes.

In particular, characterization of 5-HT$_4$ receptors and identification of pharmaceutical agents that interact with them has been the focus of significant recent activity. (See, for example, the review by Langlois and Fischmeister, *J. Med. Chem.* 2003, 46, 319-344.) 5-HT$_4$ receptor agonists are useful for the treatment of disorders of reduced motility of the gastrointestinal tract. Such disorders include irritable bowel syndrome (IBS), chronic constipation, functional dyspepsia, delayed gastric emptying, gastroesophageal reflux disease (GERD), gastroparesis, post-operative ileus, intestinal pseudo-obstruction, and drug-induced delayed transit. In addition, it has been suggested that some 5-HT$_4$ receptor agonist compounds may be used in the treatment of central nervous system disorders including cognitive disorders, behavioral disorders, mood disorders, and disorders of control of autonomic function.

Despite the broad utility of pharmaceutical agents modulating 5-HT$_4$ receptor activity, few 5-HT$_4$ receptor agonist compounds are in clinical use at present. One agent, cisapride, that was utilized extensively for treatment of motility disorders of the gastrointestinal tract was withdrawn from the market, reportedly due to cardiac side effects. Late stage clinical trials of another agent, prucalopride, have been suspended.

Accordingly, there is a need for new 5-HT$_4$ receptor agonists that achieve their desired effects with minimal side effects. Preferred agents may possess, among other properties, improved selectivity, potency, pharmacokinetic properties, and/or duration of action.

SUMMARY OF THE INVENTION

The invention provides novel compounds that possess 5-HT$_4$ receptor agonist activity. Among other properties, compounds of the invention have been found to be potent and selective 5-HT$_4$ receptor agonists. In addition, compounds of the invention have been found to exhibit favorable pharmacokinetic properties which are predictive of good bioavailability upon oral administration.

Accordingly, the invention provides a compound of formula (I):

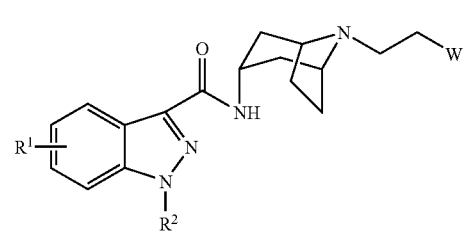

wherein:
$R^1$ is hydrogen, halo, hydroxy, $C_{1-4}$alkyl, or $C_{1-4}$alkoxy;
$R^2$ is $C_{3-4}$alkyl, or $C_{3-6}$cycloalkyl; and
W is selected from:
 (i) a group of formula (II):

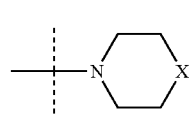

wherein X is:
 $NC(O)R^a$, wherein $R^a$ is $C_{1-3}$alkyl or tetrahydrofuranyl, wherein $C_{1-3}$ alkyl is optionally substituted with —OH or $C_{1-3}$alkoxy;
 $S(O)_2$; or
 $NS(O)_2R^b$, wherein $R^b$ is methyl, optionally substituted with —OH, $C_{1-3}$alkoxy, $C_{5-6}$cycloalkyl, or —$S(O)_2$—$C_{1-3}$alkyl;
 (ii) a group of formula (III):

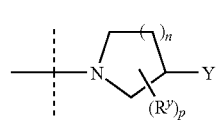

wherein:
 $R^y$ is —OH or $C_{1-3}$alkoxy;
 p is 0 or 1;
 n is 1 or 2; and
 Y is:
  $N(R^c)C(O)R^d$, wherein $R^c$ is hydrogen or $C_{1-3}$alkyl and $R^d$ is $C_{1-3}$alkyl optionally substituted with —OH or $C_{1-3}$alkoxy, or
  $N(R^e)S(O)_2R^f$, wherein $R^e$ is hydrogen and $R^f$ is $C_{1-3}$alkyl, optionally substituted with —OH, $C_{1-3}$alkoxy, $C_{5-6}$cycloalkyl, or —$S(O)_2$—$C_{1-3}$alkyl;
and
 (iii) a group of formula (IV):

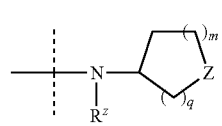

wherein:
 $R^z$ is hydrogen, $C_{1-3}$alkyl, or $C_{2-3}$alkyl substituted with —OH or $C_{1-3}$alkoxy;
 m is 1 or 2;
 q is 1 or 2, provided that the sum of m and q is not equal to 4; and Z is:
  NC(O)R$^g$, wherein R$^g$ is C$_{1-3}$alkyl, optionally substituted with —OH or C$_{1-3}$alkoxy,
  S(O)$_2$; or
  NS(O)$_2$R$^h$, wherein R$^h$ is methyl, optionally substituted with —OH, C$_{1-3}$alkoxy, C$_{5-6}$cycloalkyl, or —S(O)$_2$—C$_{1-3}$alkyl;
or a pharmaceutically-acceptable salt or solvate or stereoisomer thereof.

The invention also provides a pharmaceutical composition comprising a compound of the invention and a pharmaceutically-acceptable carrier.

The invention also provides a method of treating a disease or condition associated with 5-HT$_4$ receptor activity, e.g. a disorder of reduced motility of the gastrointestinal tract, the method comprising administering to the mammal, a therapeutically effective amount of a compound of the invention.

Further, the invention provides a method of treating a disease or condition associated with 5-HT$_4$ receptor activity in a mammal, the method comprising administering to the mammal, a therapeutically effective amount of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt or solvate or stereoisomer thereof, as a research tool for studying a biological system or sample or for discovering new 5-HT$_4$ receptor agonists, the method comprising contacting a biological system or sample with a compound of the invention and determining the effects caused by the compound on the biological system or sample.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with 5-HT$_4$ receptor activity, e.g. a disorder of reduced motility of the gastrointestinal tract, in a mammal.

DETAILED DESCRIPTION OF THE INVENTION

The invention provides novel indazole-carboxamide 5-HT$_4$ receptor agonists of formula (I), or pharmaceutically-acceptable salts or solvates or stereoisomers thereof. The following substituents and values are intended to provide representative examples of various aspects of this invention. These representative values are intended to further define such aspects and are not intended to exclude other values or limit the scope of the invention.

In a specific aspect of the invention, R$^1$ is hydrogen, halo, C$_{1-4}$alkyl, or C$_{1-4}$alkoxy.

In other specific aspects, R$^1$ is hydrogen, halo, or C$_{1-4}$alkyl; or R$^1$ is hydrogen or halo; or R$^1$ is fluoro.

In yet another specific aspect, R$^1$ is hydrogen.

In a specific aspect, R$^2$ is C$_{3-4}$alkyl or C$_{3-6}$cycloalkyl.

In another specific aspect, R$^2$ is C$_{3-4}$alkyl. Representative R$^2$ groups include n-propyl, isopropyl, n-butyl, sec-butyl, and tert-butyl.

In another specific aspect, R$^2$ is isopropyl.

In yet another specific aspect R$^2$ is cyclobutyl or cyclopentyl.

In a specific aspect, W is a group of formula (II) wherein all of the variables are defined as in formula (II).

In another specific aspect, W is a group of formula (II), wherein R$^a$ is C$_{1-3}$alkyl and R$^b$ is methyl.

In another specific aspect, W is a group of formula (II), wherein X is NC(O)R$^a$ wherein R$^a$ is defined as in formula (II). In other specific aspects, W is a group of formula (II), wherein X is NC(O)R$^a$, wherein R$^a$ is C$_{1-3}$alkyl, specifically methyl, ethyl, n-propyl, or isopropyl, or tetrahydrofuran-2-yl or tetrahydrofuran-3-yl; or R$^a$ is C$_{1-3}$alkyl.

In yet another specific aspect, W is a group of formula (I), wherein X is NC(O)CH$_3$, which forms W having the value 4-acetyl-piperazin-1-yl.

In another specific aspect, W is a group of formula (II), wherein X is S(O)$_2$.

In another specific aspect, W is a group of formula (II), wherein X is NS(O)$_2$R$^b$, wherein R$^b$ is defined as in formula (II). In another specific aspect, W is a group of formula (II), wherein X is NS(O)$_2$R$^b$, wherein R$^b$ is CH$_3$ optionally substituted with C$_{5-6}$cycloalkyl or with —S(O)$_2$—C$_{1-3}$alkyl. Representative R$^b$ values within this aspect include methyl, —CH$_2$cyclopentyl, —CH$_2$cyclohexyl, —CH$_2$SO$_2$CH$_3$, and —CH$_2$SO$_2$C$_2$H$_5$.

In yet another specific aspect, W is a group of formula (II) wherein X is NS(O)$_2$CH$_3$, which forms W having the value 4-methanesulfonyl-piperazin-1-yl.

In another specific aspect, W is a group of formula (III) wherein R$^y$ is —OH.

In another specific aspect, W is a group of formula (III) wherein R$^y$ is C$_{1-3}$alkoxy, for example R$^y$ is —OCH$_3$, —OC$_2$H$_5$, or —OC$_3$H$_7$.

In other specific aspects W is a group of formula (III) wherein p is 0, or wherein p is 1.

In other specific aspects W is a group of formula (III) wherein n is 1, i.e. W is an optionally substituted pyrrolidinyl ring; or wherein n is 2, i.e. W is an optionally substituted piperidinyl ring.

In another specific aspect, W is a group of formula (M) wherein Y is N(R$^c$)C(O)R$^d$ wherein R$^c$ and R$^d$ are defined as in formula (III). In other specific aspects, W is a group of formula (III) wherein Y is N(R$^c$)C(O)R$^d$ wherein R$^c$ is hydrogen; and wherein R$^c$ is C$_{1-3}$alkyl.

In another specific aspect, W is a group of formula (III) wherein Y is N(R$^c$)C(O)R$^d$ wherein R$^d$ is C$_{1-3}$alkyl optionally substituted with —OH or C$_{1-3}$alkoxy. Representative values of R$^d$ within this aspect include methyl, ethyl, —CH$_2$OH, and —CH(OH)CH$_3$.

In another specific aspect, W is a group of formula (III) wherein Y is NCH$_3$C(O)CH$_3$.

In yet another specific aspect, W is a group of formula (III) wherein Y is NHC(O)CH$_3$.

In another specific aspect, W is a group of formula (III) wherein Y is N(R$^e$)S(O)$_2$R$^f$ wherein R$^e$ and R$^f$ are defined as in formula (III). In another specific aspect, W is a group of formula (III) wherein Y is N(R$^e$)S(O)$_2$R$^f$ wherein I e is C$_{1-3}$alkyl optionally substituted with C$_{5-6}$cycloalkyl or with —S(O)$_2$—C$_{1-3}$alkyl. Representative values of R$^f$ within this aspect include methyl, —CH$_2$cyclopentyl, —CH$_2$cyclohexyl, —CH$_2$SO$_2$CH$_3$, and —CH$_2$SO$_2$C$_2$H$_5$.

In another specific aspect, compounds of formula (I) are compounds wherein W is a group of formula (III) wherein p is 0 and n is 1. In yet another specific aspect, compounds of formula (I) are compounds wherein W is a group of formula (III) wherein p is 0, n is 1, and Y is N(R$^c$)C(O)R$^d$.

In another specific aspect, W is a group of formula (IV), wherein R$^z$ is hydrogen.

In another specific aspect, W is a group of formula (IV), wherein R$^z$ is C$_{1-3}$alkyl, for example methyl, ethyl, and the like. In another specific aspect, W is a group of formula (IV), wherein $R^z$ is $C_{2-3}$alkyl substituted with —OH or with $C_{1-3}$alkoxy, for example $R^z$ is hydroxyethyl, methoxyethyl, and the like. In another specific aspect, W is a group of formula (IV), wherein $R^z$ is methyl.

In a specific aspect, W is a group of formula (IV) wherein m is 1.

In another specific aspect, W is a group of formula (IV) wherein m is 2.

In a specific aspect, W is a group of formula (IV) wherein q is 1.

In another specific aspect, W is a group of formula (IV) wherein q is 2.

In a specific aspect, W is a group of formula (IV) wherein Z is $NC(O)R^g$ wherein $R^g$ is defined as in formula (IV). In other specific aspects, W is a group of formula (IV) wherein Z is $NC(O)R^g$ wherein, $R^g$ is $C_{1-3}$alkyl, optionally substituted with —OH; or $R^g$ is methyl.

In a specific aspect, W is a group of formula (IV) wherein Z is $S(O)_2$.

In a specific aspect, W is a group of formula (IV) wherein Z is $NS(O)_2R^h$, wherein $R^h$ is defined as in formula (IV). In other specific aspects, W is a group of formula (IV) wherein Z is $NS(O)_2R^h$ wherein $R^h$ is methyl optionally substituted with $C_{5-6}$cycloalkyl or with —$S(O)_2$—$C_{1-3}$alkyl. Representative values of $R^h$ include methyl, —$CH_2$cyclopentyl, —$CH_2$cyclohexyl, —$CH_2SO_2CH_3$, and —$CH_2SO_2C_2H_5$. In yet another other specific aspect, W is a group of formula (IV) wherein Z is $NS(O)_2CH_3$.

In another specific aspect, compounds of formula (I) are compounds wherein W is a group of formula (IV) wherein m is 1 and q is 1. In yet another specific aspect, compounds of formula (I) are compounds wherein W is a group of formula (IV) wherein m is 1, q is 1, and $R^z$ is methyl.

In one aspect, the invention provides a compound of formula (I) wherein $R^1$ is hydrogen or halo; $R^2$ is isopropyl or $C_{4-5}$cycloalkyl; and W is defined as in formula (I).

In another aspect, the invention provides a compound of formula (I) wherein:
 $R^1$ is hydrogen or halo;
 $R^2$ is $C_{3-4}$alkyl or $C_{4-5}$cycloalkyl; and
 W is selected from:
  (i) a group of formula (II) wherein X is $NC(O)CH_3$, $S(O)_2$, or $NS(O)_2CH_3$;
  (ii) a group of formula (III) wherein p is 0, n is 1, and Y is $NCH_3C(O)CH_3$; and
  (iii) a group of formula (IV) wherein $R^z$ is methyl, m is 1, q is 1, and Z is $NC(O)CH_3$, $S(O)_2$, or $NS(O)_2CH_3$.

In another aspect, the invention provides a compound of formula (I) wherein $R^1$ is hydrogen or halo; $R^2$ is $C_{3-4}$alkyl or $C_{4-5}$cycloalkyl; and W is a group of formula (II) wherein X is $NC(O)CH_3$; $S(O)_2$; or $NS(O)_2CH_3$.

In another aspect, the invention provides a compound of formula (I) which is a compound of formula (V):

(V)

wherein:
 $R^1$, $R^2$, and X take any of the generic, specific, or exemplary values described above.

In yet another aspect, the invention provides a group of compounds of formula (VI):

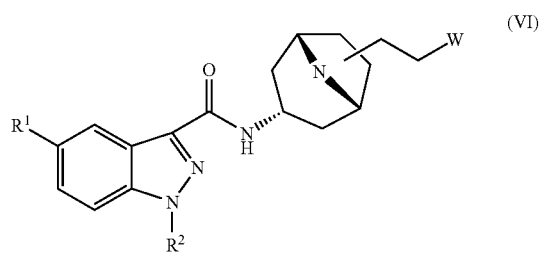

(VI)

wherein $R^1$, $R^2$, and W take the values shown in Table I.

TABLE I

| Example No. | $R^1$ | $R^2$ | W |
|---|---|---|---|
| 1 | H | i-Pr | piperazine-N-C(O)CH$_3$ |
| 2 | H | i-Pr | piperazine-N-C(O)-tetrahydrofuran-2-yl |
| 3 | H | i-Pr | thiomorpholine-1,1-dioxide |
| 4 | H | i-Pr | piperazine-N-S(O)$_2$CH$_3$ |
| 5 | H | i-Pr | piperazine-N-S(O)$_2$CH$_2$cyclohexyl |
| 6 | H | i-Pr | piperazine-N-S(O)$_2$CH$_2$S(O)$_2$CH$_3$ |
| 7 | H | i-Pr | pyrrolidine-N(CH$_3$)C(O)CH$_3$ |
| 8 | H | i-Pr | pyrrolidine-NHC(O)CH$_3$ |

TABLE I-continued

| Example No. | R¹ | R² | W |
|---|---|---|---|
| 9 | H | i-Pr | (1-substituted pyrrolidin-3-yl)-NHC(O)CH₃ |
| 10 | H | i-Pr | (1-substituted pyrrolidin-3-yl)-NHC(O)CH₃ |
| 11 | H | i-Pr | (1-substituted pyrrolidin-3-yl)-NHC(O)CH(OH)CH₃ |
| 12 | H | i-Pr | (1-substituted-4-hydroxypyrrolidin-3-yl)-NHC(O)CH₃ |
| 13 | H | i-Pr | (1-substituted pyrrolidin-3-yl)-NHS(O)₂Et |
| 14 | H | i-Pr | (1-substituted pyrrolidin-3-yl)-NHS(O)₂CH₂-cyclohexyl |
| 15 | H | i-Pr | (1-substituted piperidin-3-yl)-N(CH₃)C(O)CH₃ |
| 16 | H | i-Pr | (1-substituted piperidin-3-yl)-NHC(O)CH₃ |
| 17 | H | i-Pr | (1-substituted piperidin-3-yl)-NHS(O)₂CH₃ |
| 18 | H | i-Pr | (1-substituted piperidin-3-yl)-NHS(O)₂CH₃ |
| 19 | H | i-Pr | (1-substituted piperidin-3-yl)-NHS(O)₂Et |
| 20 | H | i-Pr | (1-substituted piperidin-3-yl)-NHS(O)₂CH₂S(O)₂CH₃ |
| 21 | H | i-Pr | N-methyl-N-(1-acetylpyrrolidin-3-yl) |
| 22 | H | i-Pr | N-methyl-N-(1-acetylpyrrolidin-3-yl) |
| 23 | H | i-Pr | N-methyl-N-(1-acetylpyrrolidin-3-yl) |
| 24 | H | i-Pr | N-methyl-N-(1-methylsulfonylpyrrolidin-3-yl) |
| 25 | H | i-Pr | N-methyl-N-(1-methylsulfonylpyrrolidin-3-yl) |
| 26 | H | i-Pr | N-methyl-N-(1,1-dioxotetrahydrothiophen-3-yl) |
| 27 | H | i-Pr | N-(2-hydroxyethyl)-N-(1,1-dioxotetrahydrothiophen-3-yl) |
| 28 | H | i-Pr | N-methyl-N-(1-acetylpiperidin-3-yl) |
| 29 | H | i-Pr | N-methyl-N-(1,1-dioxotetrahydrothiopyran-4-yl) |

TABLE I-continued

| Example No. | R¹ | R² | W |
|---|---|---|---|
| 30 | H | i-Pr | piperidine with N-methyl and N-SO₂Me substituents |
| 31 | F | i-Pr | N-acetyl piperazine |
| 32 | H | n-Pr | N-acetyl piperazine |
| 33 | H | n-Bu | N-acetyl piperazine |
| 34 | H | cyclobutyl | N-acetyl piperazine |
| 35 | H | cyclopentyl | N-acetyl piperazine |
| 36 | H | i-Pr | pyrrolidine with N(Me)C(O)Me |
| 37 | H | i-Pr | pyrrolidine with N(Me)C(O)Me (stereo) |
| 38 | H | i-Pr | pyrrolidine with N(Me)SO₂Me |
| 39 | H | i-Pr | tetrahydrothiophene dioxide |
| 40 | H | i-Pr | tetrahydrothiophene dioxide (stereo) |

The chemical naming conventions used herein are illustrated for the compound of Example 1:

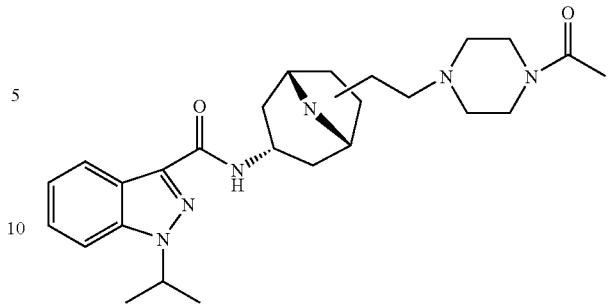

which is designated 1-isopropyl-1H-indazole-3-carboxylic acid {(1S,3R,5R)-8-[2-(4-acetyl-piperazin-1-yl)ethyl]-8-azabicyclo[3.2.1]oct-3-yl}amide, according to the AutoNom software, provided by MDL Information Systems, GmbH (Frankfurt, Germany). The designation (1S,3R,5R) describes the relative orientation of the bonds associated with the bicyclic ring system that are depicted as solid and dashed wedges. The compound is alternatively denoted as N-[(3-endo)-8-[2-(4-acetyl-piperazin-1-yl)ethyl]-8-azabicyclo[3.2.1]oct-3-yl]-1-(1-methylethyl)-1H-indazole-3-carboxamide. In all of the compounds depicted in Table I above, the indazole carboxamide is endo to the azabicyclooctyl group.

Particular mention may be made of the following compounds:

1-isopropyl-1H-indazole-3-carboxylic acid {(1S,3R,5R)-8-[2-(4-acetylpiperazin-1-yl)ethyl]-8-azabicyclo[3.2.1]oct-3-yl}amide;

1-isopropyl-1H-indazole-3-carboxylic acid {(1S,3R,5R)-8-[2-(1,1-dioxo-1$\lambda^6$-thiomorpholin-4-yl)ethyl]-8-azabicyclo[3.2.1]oct-3-yl}amide;

1-isopropyl-1H-indazole-3-carboxylic acid {(1S,3R,5R)-8-[2-(4-methanesulfonyl-piperazin-1-yl)ethyl]-8-azabicyclo[3.2.1]oct-3-yl}amide;

1-isopropyl-1H-indazole-3-carboxylic acid {(1S,3R,5R)-8-[2-(3-(acetyl-methylamino)pyrrolidin-1-yl)ethyl]-8-azabicyclo[3.2.1]oct-3-yl}amide;

1-isopropyl-1H-indazole-3-carboxylic acid {(1S,3R,5R)-8-[2-((R)-3-(acetyl-methylamino)pyrrolidin-1-yl)ethyl]-8-azabicyclo[3.2.1]oct-3-yl}amide;

1-isopropyl-1H-indazole-3-carboxylic acid {(1S,3R,5R)-8-[2-((S)-3-(acetyl-methylamino)pyrrolidin-1-yl)-ethyl]-8-azabicyclo[3.2.1]oct-3-yl}amide;

1-isopropyl-1H-indazole-3-carboxylic acid {(1S,3R,5R)-8-[2-[(1-acetyl-pyrrolidin-3-yl)-methylamino]ethyl]-8-azabicyclo[3.2.1]oct-3-yl}amide;

1-isopropyl-1H-indazole-3-carboxylic acid {(1S,3R,5R)-8-[2-[((R)-1-acetyl-pyrrolidin-3-yl)methylamino]ethyl]-8-azabicyclo[3.2.1]oct-3-yl}amide;

1-isopropyl-1H-indazole-3-carboxylic acid {(1S,3R,5R)-8-[2-[((S)-1-acetyl-pyrrolidin-3-yl)methylamino]ethyl]-8-aza-bicyclo[3.2.1]oct-3-yl}amide;

1-isopropyl-1H-indazole-3-carboxylic acid ((1S,3R,5R)-8-{2-[(1-methanesulfonyl-pyrrolidin-3-yl)methylamino]ethyl}-8-azabicyclo[3.2.1]oct-3-yl)amide;

1-isopropyl-1H-indazole-3-carboxylic acid ((1S,3R,5R)-8-{2-[((R)-1-methanesulfonylpyrrolidin-3-yl)methylamino]ethyl}-8-azabicyclo[3.2.1]oct-3-yl)amide;

1-isopropyl-1H-indazole-3-carboxylic acid ((1S,3R,5R)-8-{2-[((S)-1-methanesulfonylpyrrolidin-3-yl)methylamino]ethyl}-8-azabicyclo[3.2.1]oct-3-yl)amide;

1-isopropyl-1H-indazole-3-carboxylic acid {(1S,3R,5R)-8-[2-((1,1-dioxo-tetrahydro-1$\lambda^6$-thiophen-3-yl)methylamino)ethyl]-8-azabicyclo[3.2.1]oct-3-yl}amide;

1-isopropyl-1H-indazole-3-carboxylic acid {(1S,3R,5R)-8-[2-((R)-(1,1-dioxo-tetrahydro-1λ⁶-thiophen-3-yl)methylamino)ethyl]-8-azabicyclo[3.2.1]oct-3-yl}amide; and 1-isopropyl-1H-indazole-3-carboxylic acid {(1S,3R,5R)-8-[2-((S)-(1,1-dioxo-tetrahydro-1λ⁶-thiophen-3-yl)methylamino)ethyl]-8-azabicyclo[3.2.1]oct-3-yl}amide;

As illustrated above, the compounds of the invention may contain a chiral center. Accordingly, the invention includes racemic mixtures, pure stereoisomers, and stereoisomer-enriched mixtures of such isomers, unless otherwise indicated. When a particular stereoisomer is shown, it will be understood by those skilled in the art, that minor amounts of other stereoisomers may be present in the compositions of the invention unless otherwise indicated, provided that the utility of the composition as a whole is not eliminated by the presence of such other isomers.

Definitions

When describing the compounds, compositions and methods of the invention, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl, ethyl, n-propyl (n-Pr), isopropyl (i-Pr), n-butyl (n-Bu), sec-butyl, isobutyl, tert-butyl, n-pentyl, n-hexyl, n-heptyl, n-octyl, n-nonyl, n-decyl and the like.

The term "alkoxy" means a monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl, cycloheptyl, cyclooctyl, and the like.

The term "halo" means fluoro, chloro, bromo or iodo.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes:

(a) preventing the disease, disorder, or medical condition from occurring, i.e., prophylactic treatment of a patient;
(b) ameliorating the disease, disorder, or medical condition, i.e., eliminating or causing regression of the disease, disorder, or medical condition in a patient;
(c) suppressing the disease, disorder, or medical condition, i.e., slowing or arresting the development of the disease, disorder, or medical condition in a patient; or
(d) alleviating the symptoms of the disease, disorder, or medical condition in a patient.

The term "pharmaceutically-acceptable salt" means a salt prepared from an acid or base which is acceptable for administration to a patient, such as a mammal. Such salts can be derived from pharmaceutically-acceptable inorganic or organic acids and from pharmaceutically-acceptable bases. Typically, pharmaceutically-acceptable salts of compounds of the present invention are prepared from acids.

Salts derived from pharmaceutically-acceptable acids include, but are not limited to, acetic, adipic, benzenesulfonic, benzoic, camphorsulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, propionic, salicylic, succinic, sulfuric, tartaric, p-toluenesulfonic, xinafoic (1-hydroxy-2-naphthoic acid), naphthalene-1,5-disulfonic acid and the like.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of formula (I).

The term "amino-protecting group" means a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In one method of synthesis, compounds of formula (I) are prepared as illustrated in Scheme A. (The substituents and variables shown in the following schemes have the definitions provided above unless otherwise indicated.)

Scheme A

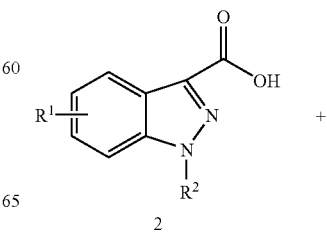

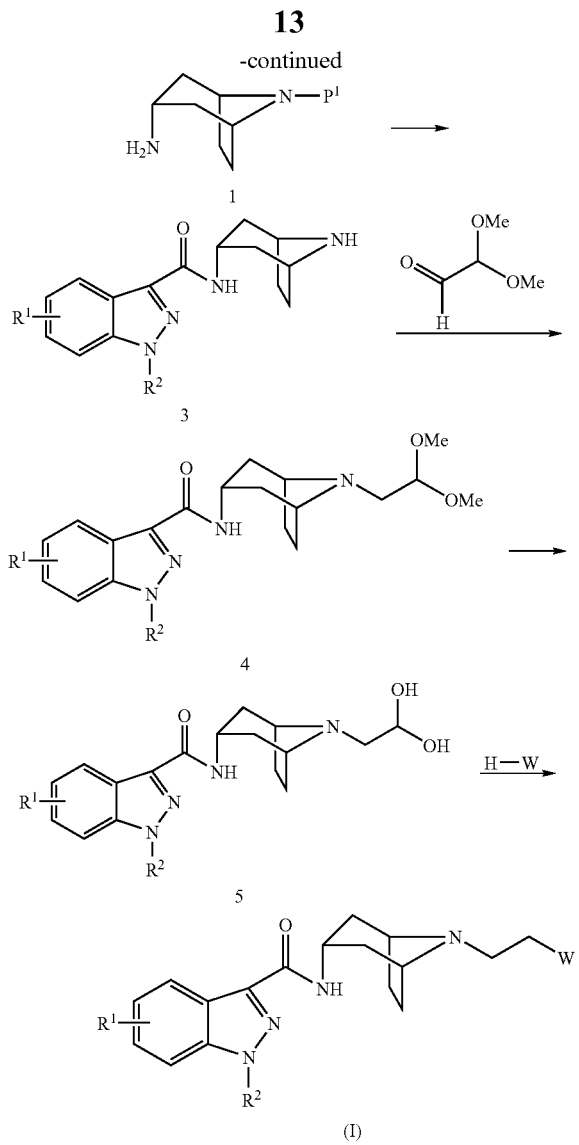

where P¹ represents an amino-protecting group such as tert-butoxycarbonyl (Boc) or benzyloxycarbonyl (Cbz).

As shown in Scheme A, the protected aminoazabicyclooctane, or commonly, aminotropane 1 is first reacted with the substituted 1H-indazole carboxylic acid 2. Typically, this reaction is conducted by first converting 2 to an acid chloride by contacting 2 with at least one equivalent, typically between about 1 and about 2 equivalents of an activating agent, such as thionyl chloride or oxalyl chloride in an aromatic diluent, such as toluene, benzene, xylene, or the like. The reaction is typically conducted at a temperature ranging from about 80° C. to about 120° C. for about 15 minutes to about 2 hours, or until the reaction is substantially complete.

The acid chloride solution is typically added to a biphasic mixture of about 1 equivalent of the aminotropane 1 to form a protected intermediate, which is extracted by standard procedures. The biphasic mixture of 1 is generally prepared by dissolving 1 in an aromatic diluent, such as used above, and adding an aqueous solution containing an excess of base, such as sodium hydroxide or potassium hydroxide, for example about 2 to 5 equivalents of base.

Alternatively, the amide coupling of intermediate 1 with the carboxylic acid 2 can be performed by converting 2 to an activated ester, such as an N-hydroxy succinimide (NHS) ester or a p-nitrophenyl ester, or an acid imidazole, which is then reacted with aminotropane 1. In yet another alternative, the carboxylic acid 2 is reacted with intermediate 1 in the presence of a coupling agent such as 1,3 dicyclohexylcarbodiimide (DCC), 1-(3-dimethylaminopropyl)-3-ethylcarbodiimide (EDC), or benzotriazol-1-yloxytripyrrolidino-phosphonium hexafluorophosphate (PyBop), optionally combined with 1-hydroxy-7-azabenzotriazole (HOAt).

The protecting group P¹ is removed by standard procedures to provide an intermediate of formula 3. For example, the protecting group Boc, is typically removed by treatment with an acid, such as trifluoroacetic acid. The protecting group Cbz, for example, is conveniently removed by hydrogenolysis over a suitable metal catalyst such as palladium on carbon.

Intermediate 3 is then reductively N-alkylated by reaction with dimethoxyacetaldehyde to provide an intermediate of formula 4. This reaction is typically conducted by contacting 3 with between about 1 and about 4 equivalents of dimethoxyacetaldehyde in an inert diluent in the presence of between about 1 and about 2 equivalents of a reducing agent. The reaction is typically conducted at ambient temperature for about 1 to about 2 hours, or until the reaction is substantially complete. Suitable inert diluents include dichloromethane, trichloromethane, 1,1,2,2-tetrachloroethane, and the like. Typical reducing agents include sodium triacetoxyborohydride, sodium borohydride, and sodium cyanoborohydride. The product 4 is isolated by standard procedures.

Next, the dimethoxyethyl intermediate 4 is hydrolyzed in an aqueous solution of a strong acid, for example 3N or 6N HCl, to provide the dihydroxyethyl intermediate 5. It will be understood that while intermediate 5 is shown in Scheme A in the form of an aldehyde hydrate, intermediate 5 can equivalently be depicted in the form of an aldehyde. The reaction is typically conducted at a temperature in the range of about 50° C. to about 100° C. for about 15 minutes to about 2 hours, or until the reaction is substantially complete. The product 5 can be isolated in salt form, for example as the HCl salt, or as the neutral species after alkaline extraction. Alternatively, the crude intermediate 5 can be used in the final step without further manipulation.

Finally the intermediate 5 is reductively coupled with the primary or secondary amine of the formula H—W, to provide the product of formula (I). Typically, a solution is prepared of between about 1 and about 3 equivalents, for example about 2 equivalents, of the amine and a reducing agent, such as sodium triacetoxyborohydride or the like, in an inert diluent such as dichloromethane. The intermediate 5 is added to the amine mixture. The reaction is typically conducted at ambient temperature for about 15 minutes to about 2 hours, or until the reaction is substantially complete. The crude product of formula (I) is extracted by conventional procedures. The product can be purified in salt form by crystallization from an inert diluent, for example, ethanol, isopropyl alcohol, methanol, acetonitrile, dichloroethane, or mixtures thereof.

Alternatively, compounds of formula (I) can be prepared by N-alkylating a compound of formula (I) in which R² is hydrogen, which can be prepared according to Scheme A. The N-alkylation reaction is typically conducted by contacting a compound of formula (I) in which R² is hydrogen with between about 1 and about 4 equivalents of a compound of the formula L-R² in which L is a leaving group such as iodo or bromo. This reaction is typically conducted in a polar aprotic solvent such as dimethylformamide in the presence of between about 2 and about 4 equivalents of strong base, such as potassium tert-butoxide. Typically, the reaction is performed at a temperature of between about 60 and about 100°

C. for between about 6 and about 24 hours, or until the reaction is substantially complete.

The protected aminotropane 1 employed in the reactions described in this application is prepared from readily available starting materials. For example, when the protecting group P¹ is Boc, the protected endo aminotropane 1' is prepared by the procedure illustrated in Scheme B.

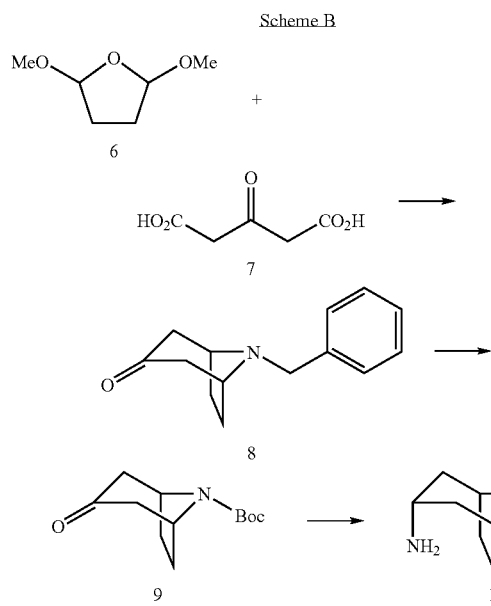

As described in detail in Example 1a below, to prepare the protected intermediate 1', first, 2,5-dimethoxy tetrahydrofuran 6 is contacted with between about 1 and 2 equivalents, preferably about 1.5 equivalents of benzyl amine and a slight excess, for example about 1.1 equivalents, of 1,3-acetonedicarboxylic acid 7 in an acidic aqueous solution in the presence of a buffering agent such as sodium hydrogen phosphate. The reaction mixture is heated to between about 60 and about 100° C. to ensure decarboxylation of any carboxylated intermediates in the product, 8-benzyl-8-azabicyclo[3.2.1]octan-3-one 8, commonly N-benzyltropanone.

The intermediate 8 is typically reacted with a slight excess of di-tert-butyl dicarbonate (commonly (Boc)₂O), for example, about 1.1 equivalents, under a hydrogen atmosphere in the presence of a transition metal catalyst to provide the Boc protected intermediate 9,3-oxo-8-azabicyclo[3.2.1]octane-8-carboxylic acid tert-butyl ester. The reaction is typically conducted at ambient temperature for about 12 to about 72 hours. Finally, intermediate 9 is contacted with a large excess, for example at least about 25 equivalents, of ammonium formate in an inert diluent, such as methanol, in the presence of a transition metal catalyst to provide the product 1' in the endo configuration with high stereospecificity, for example endo to exo ratio of >99. The reaction is typically conducted at ambient temperature for about 12 to about 72 hours or until the reaction is substantially complete. It is advantageous to add the ammonium formate reagent in portions. For example, intermediate 9 is contacted with an initial portion of ammonium formate of about 15 to about 25 equivalents. After an interval of about 12 to about 36 hours, an additional portion of about 5 to about 10 equivalents of ammonium formate is added. The subsequent addition can be repeated after a similar interval. The product 1' can be purified by conventional procedures, such as alkaline extraction.

The 1H-indazole carboxylic acid 2 is readily prepared by procedures known in the art, and described, for example, in the literature in Harada et al. *Chem. and Pharm Bull.* 1995, 43, 1912-30 and in the examples below.

The amines H—W are available commercially or are readily prepared by standard procedures from common starting materials.

Further details regarding specific reaction conditions and other procedures for preparing representative compounds of the invention or intermediates thereto are described in the examples below.

Accordingly, in a method aspect, the invention provides a process for preparing a compound of formula (I), or a salt or stereoisomer or protected derivative thereof, the process comprising reacting a compound of formula 5 with an amine of the formula H—W to provide a compound of formula (I), or a salt or stereoisomer or protected derivative thereof.

The invention further provides a compound of formula 5, or a salt or stereoisomer or protected derivative thereof, wherein R¹ and R² are defined as in formula (I).

In an alternative method of synthesis, compounds of formula (I) are prepared by coupling the substituted 1H-indazole carboxylic acid 2 with an intermediate of formula 10 as illustrated in Scheme C.

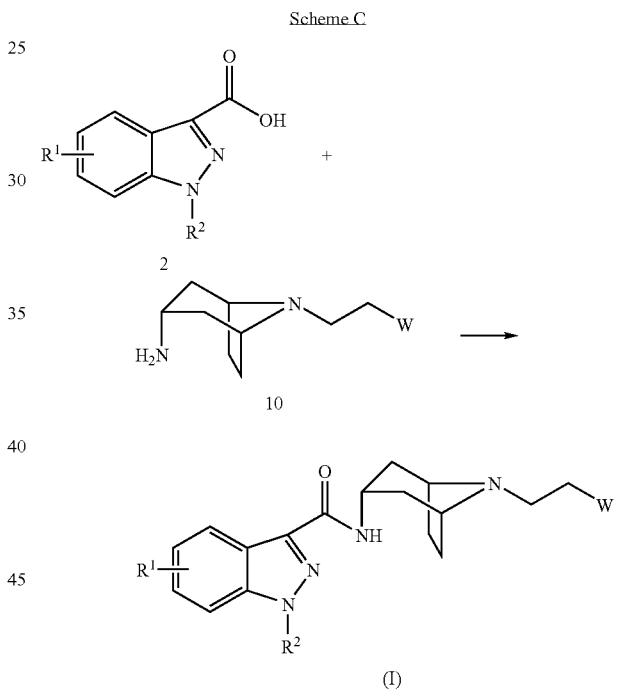

The reaction of Scheme C is typically conducted under the amide coupling conditions described above for the reaction of the carboxylic acid 2 with intermediate 1.

Intermediates of formula 10 can be prepared by deprotecting an intermediate of formula 11

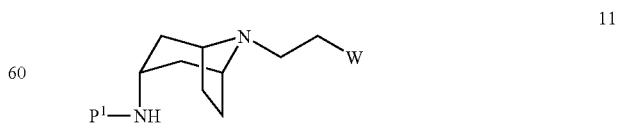

where P¹ represents an amino-protecting group.

Intermediates of formula 11 can be prepared from readily available starting materials using procedures analogous to the alkylation, reductive amination, and other reactions described above and/or using alternative reactions will known to those skilled in the art. Exemplary process routes (i) through (v) for the preparation of intermediate 11 are illustrated in Scheme D:

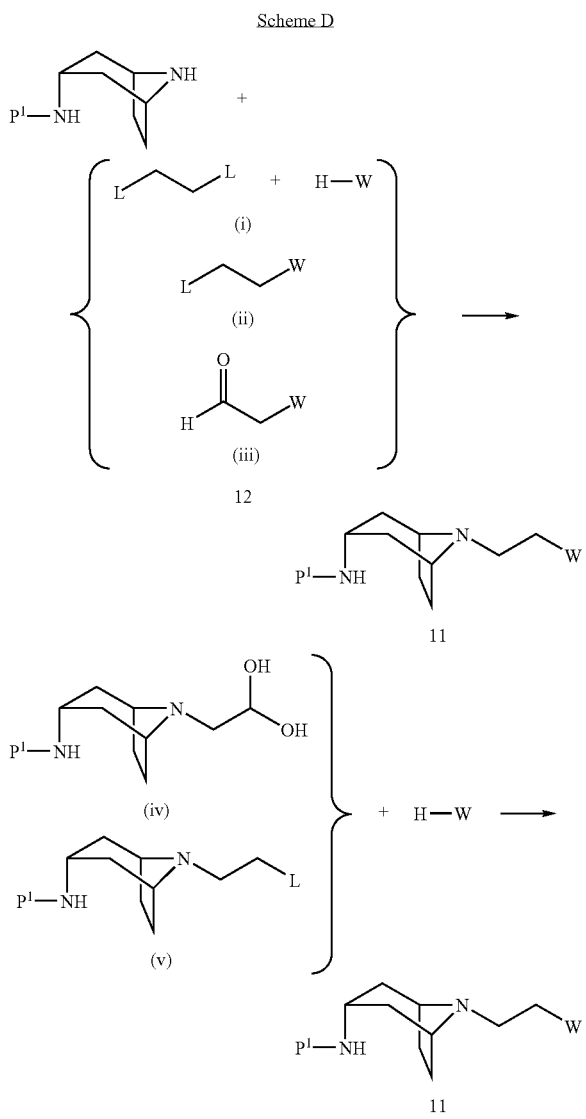

where L denotes a leaving group such as bromo or iodo.

In yet another alternative method of synthesis, compounds of formula (I) are prepared by coupling an intermediate of formula 3, depicted in Scheme A, with an intermediate of formula 12. It will be understood that while intermediate 12 is shown in Scheme D in the form of an aldehyde, intermediate 12 can equivalently be depicted in the form of an aldehyde hydrate.

Pharmaceutical Compositions

The indazole-carboxamide compounds of the invention are typically administered to a patient in the form of a pharmaceutical composition. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a compound of formula (I) or a pharmaceutically acceptable salt thereof. Optionally, such pharmaceutical compositions may contain other therapeutic and/or formulating agents if desired.

The pharmaceutical compositions of the invention typically contain a therapeutically effective amount of a compound of the present invention or a pharmaceutically-acceptable salt thereof. Typically, such pharmaceutical compositions will contain from about 0.1 to about 95% by weight of the active agent; including from about 1 to about 70% by weight; such as from about 5 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially-available from, for example, Sigma, P.O. Box 14508, St. Louis, Mo. 63178. By way of further illustration, conventional formulation techniques are described in Remington: The Science and Practice of Pharmacy, 20$^{th}$ Edition, Lippincott Williams & White, Baltimore, Md. (2000); and H. C. Ansel et al., Pharmaceutical Dosage Forms and Drug Delivery Systems, 7$^{th}$ Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, such as microcrystalline cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions.

The pharmaceutical compositions of the invention are typically prepared by thoroughly and intimately mixing or blending a compound of the invention with a pharmaceutically-acceptable carrier and one or more optional ingredients. If necessary or desired, the resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

In a preferred embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise a compound of the present invention as the active ingredient and one or more pharmaceutically-acceptable carriers, such as sodium citrate or dicalcium phosphate. Optionally or alternatively, such solid dosage forms may also comprise: (1) fillers or extenders, such as starches, microcrystalline cellulose, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas.

Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, a compound of the invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The following formulations illustrate representative pharmaceutical compositions of the present invention:

FORMULATION EXAMPLE A

Hard gelatin capsules for oral administration are prepared as follows:

| Ingredients | Amount |
| --- | --- |
| Compound of the invention | 50 mg |
| Lactose (spray-dried) | 200 mg |
| Magnesium stearate | 10 mg |

Representative Procedure: The ingredients are thoroughly blended and then loaded into a hard gelatin capsule (260 mg of composition per capsule).

FORMULATION EXAMPLE B

Hard gelatin capsules for oral administration are prepared as follows:

| Ingredients | Amount |
| --- | --- |
| Compound of the invention | 20 mg |
| Starch | 89 mg |
| Microcrystalline cellulose | 89 mg |
| Magnesium stearate | 2 mg |

Representative Procedure: The ingredients are thoroughly blended and then passed through a No. 45 mesh U.S. sieve and loaded into a hard gelatin capsule (200 mg of composition per capsule).

FORMULATION EXAMPLE C

Capsules for oral administration are prepared as follows:

| Ingredients | Amount |
| --- | --- |
| Compound of the invention | 10 mg |
| Polyoxyethylene sorbitan monooleate | 50 mg |
| Starch powder | 250 mg |

Representative Procedure: The ingredients are thoroughly blended and then loaded into a gelatin capsule (310 mg of composition per capsule).

FORMULATION EXAMPLE D

Tablets for oral administration are prepared as follows:

| Ingredients | Amount |
| --- | --- |
| Compound of the invention | 5 mg |
| Starch | 50 mg |
| Microcrystalline cellulose | 35 mg |
| Polyvinylpyrrolidone (10 wt. % in water) | 4 mg |
| Sodium carboxymethyl starch | 4.5 mg |
| Magnesium stearate | 0.5 mg |
| Talc | 1 mg |

Representative Procedure: The active ingredient, starch and cellulose are passed through a No. 45 mesh U.S. sieve and mixed thoroughly. The solution of polyvinylpyrrolidone is mixed with the resulting powders, and this mixture is then passed through a No. 14 mesh U.S. sieve. The granules so produced are dried at 50-60° C. and passed through a No. 18 mesh U.S. sieve. The sodium carboxymethyl starch, magnesium stearate and talc (previously passed through a No. 60 mesh U.S. sieve) are then added to the granules. After mixing, the mixture is compressed on a tablet machine to afford a tablet weighing 100 mg.

FORMULATION EXAMPLE E

Tablets for oral administration are prepared as follows:

| Ingredients | Amount |
| --- | --- |
| Compound of the invention | 25 mg |
| Microcrystalline cellulose | 400 mg |
| Silicon dioxide fumed | 10 mg |
| Stearic acid | 5 mg |

Representative Procedure: The ingredients are thoroughly blended and then compressed to form tablets (440 mg of composition per tablet).

FORMULATION EXAMPLE F

Single-scored tablets for oral administration are prepared as follows:

| Ingredients | Amount |
| --- | --- |
| Compound of the invention | 15 mg |
| Cornstarch | 50 mg |
| Croscarmellose sodium | 25 mg |
| Lactose | 120 mg |
| Magnesium stearate | 5 mg |

Representative Procedure: The ingredients are thoroughly blended and compressed to form a single-scored tablet (215 mg of compositions per tablet).

FORMULATION EXAMPLE G

A suspension for oral administration is prepared as follows:

| Ingredients | Amount |
| --- | --- |
| Compound of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 10 mg of active ingredient per 10 mL of suspension.

FORMULATION EXAMPLE H

A dry powder for administration by inhalation is prepared as follows:

| Ingredients | Amount |
| --- | --- |
| Compound of the invention | 1.0 mg |
| Lactose | 25 mg |

Representative Procedure: The active ingredient is micronized and then blended with lactose. This blended mixture is then loaded into a gelatin inhalation cartridge. The contents of the cartridge are administered using a powder inhaler.

FORMULATION EXAMPLE I

A dry powder for administration by inhalation in a metered dose inhaler is prepared as follows:
Representative Procedure: A suspension containing 5 wt. % of a compound of the invention and 0.1 wt. % lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

FORMULATION EXAMPLE J

An injectable formulation is prepared as follows:

| Ingredients | Amount |
| --- | --- |
| Compound of the invention | 0.2 g |
| Sodium acetate buffer solution (0.4 M) | 40 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

FORMULATION EXAMPLE K

Capsules for oral administration are prepared as follows:

| Ingredients | Amount |
| --- | --- |
| Compound of the Invention | 4.05 mg |
| Microcrystalline cellulose (Avicel PH 103) | 259.2 mg |
| Magnesium stearate | 0.75 mg |

Representative Procedure: The ingredients are thoroughly blended and then loaded into a gelatin capsule (Size #1, White, Opaque) (264 mg of composition per capsule).

FORMULATION EXAMPLE L

Capsules for oral administration are prepared as follows:

| Ingredients | Amount |
| --- | --- |
| Compound of the Invention | 8.2 mg |
| Microcrystalline cellulose (Avicel PH 103) | 139.05 mg |
| Magnesium stearate | 0.75 mg |

Representative Procedure: The ingredients are thoroughly blended and then loaded into a gelatin capsule (Size #1, White, Opaque) (148 mg of composition per capsule).

It will be understood that any form of the compounds of the invention, (i.e. free base, pharmaceutical salt, or solvate) that is suitable for the particular mode of administration, can be used in the pharmaceutical compositions discussed above.

Utility

The indazole-carboxamide compounds of the invention are 5-HT$_4$ receptor agonists and therefore are expected to be useful for treating medical conditions mediated by 5-HT$_4$ receptors or associated with 5-HT$_4$ receptor activity, i.e. medical conditions which are ameliorated by treatment with a 5-HT$_4$ receptor agonist. Such medical conditions include, but are not limited to, irritable bowel syndrome (IBS), chronic constipation, functional dyspepsia, delayed gastric emptying, gastroesophageal reflux disease (GERD), gastroparesis, diabetic and idiopathic gastropathy, post-operative ileus, intestinal pseudo-obstruction, and drug-induced delayed transit. In addition, it has been suggested that some 5-HT$_4$ receptor agonist compounds may be used in the treatment of central nervous system disorders including cognitive disorders, behavioral disorders, mood disorders, and disorders of control of autonomic function.

In particular, the compounds of the invention increase motility of the gastrointestinal (GI) tract and thus are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a compound of the invention.

When used to treat disorders of reduced motility of the GI tract or other conditions mediated by 5-HT$_4$ receptors, the compounds of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by 5-HT$_4$ receptors are expected to range from about 0.0007 to about 20 mg/kg/day of active agent, including from about 0.0007 to about 1 mg/kg/day. For an average 70 kg human, this would amount to from about 0.05 to about 70 mg per day of active agent.

In one aspect of the invention, the compounds of the invention are used to treat chronic constipation. When used to treat chronic constipation, the compounds of the invention will typically be administered orally in a single daily dose or in multiple doses per day. The dose for treating chronic constipation is expected to range from about 0.05 to about 70 mg per day.

In another aspect of the invention, the compounds of the invention are used to treat irritable bowel syndrome. When used to treat constipation-predominant irritable bowel syndrome, the compounds of the invention will typically be administered orally in a single daily dose or in multiple doses per day. The dose for treating constipation-predominant irritable bowel syndrome is expected to range from about 0.05 to about 70 mg per day.

In another aspect of the invention, the compounds of the invention are used to treat diabetic gastroparesis. When used to treat diabetic gastroparesis, the compounds of the invention will typically be administered orally in a single daily dose or in multiple doses per day. The dose for treating diabetic gastroparesis is expected to range from about 0.05 to about 70 mg per day.

In yet another aspect of the invention, the compounds of the invention are used to treat functional dyspepsia. When used to treat functional dyspepsia, the compounds of the invention will typically be administered orally in a single daily dose or in multiple doses per day. The dose for treating functional dyspepsia is expected to range from about 0.05 to about 70 mg per day.

The invention also provides a method of treating a mammal having a disease or condition associated with 5-HT$_4$ receptor activity, the method comprising administering to the mammal a therapeutically effective amount of a compound of the invention or of a pharmaceutical composition comprising a compound of the invention.

As described above, compounds of the invention are 5-HT$_4$ receptor agonists. The invention further provides, therefore, a method of agonizing a 5-HT$_4$ receptor in a mammal, the method comprising administering a compound of the invention to the mammal. In addition, the compounds of the invention are also useful as research tools for investigating or studying biological systems or samples having 5-HT$_4$ receptors, or for discovering new 5-HT$_4$ receptor agonists. Moreover, since compounds of the invention exhibit binding selectivity for 5-HT$_4$ receptors as compared with binding to receptors of other 5-HT subtypes, particularly 5-HT$_3$ receptors, such compounds are particularly useful for studying the effects of selective agonism of 5-HT$_4$ receptors in a biological system or sample. Any suitable biological system or sample having 5-HT$_4$ receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.) and the like.

In this aspect of the invention, a biological system or sample comprising a 5-HT$_4$ receptor is contacted with a 5-HT$_4$ receptor-agonizing amount of a compound of the invention. The effects of agonizing the 5-HT$_4$ receptor are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of analogs of guanosine triphosphate (GTP), such as [$^{35}$S]GTPγS (guanosine 5'-O-(γ-thio) triphosphate) or GTP-Eu, into isolated membranes via receptor catalyzed exchange of GTP analogs for GDP analogs, ligand-mediated changes in free intracellular calcium ions (measured, for example, with a fluorescence-linked imaging plate reader or FLIPR® from Molecular Devices, Inc.), and measurement of mitogen activated protein kinase (MAPK) activation. A compound of the invention may agonize or increase the activation of 5-HT$_4$ receptors in any of the functional assays listed above, or assays of a similar nature. A 5-HT$_4$ receptor-agonizing amount of a compound of the invention will typically range from about 1 nanomolar to about 500 nanomolar.

Additionally, the compounds of the invention can be used as research tools for discovering new 5-HT$_4$ receptor agonists. In this embodiment, 5-HT$_4$ receptor binding or functional data for a test compound or a group of test compounds is compared to the 5-HT$_4$ receptor binding or functional data for a compound of the invention to identify test compounds that have superior binding or functional activity, if any. This aspect of the invention includes, as separate embodiments, both the generation of comparison data (using the appropriate assays) and the analysis of the test data to identify test compounds of interest.

Among other properties, compounds of the invention have been found to be potent agonists of the 5-HT$_4$ receptor and to exhibit substantial selectivity for the 5-HT$_4$ receptor subtype over the 5-HT$_3$ receptor subtype in radioligand binding assays. Further, compounds of the invention have demonstrated superior pharmacokinetic properties in a rat model. Compounds of the invention are thus expected to be highly bioavailable upon oral administration. In addition, these compounds have been shown not to inhibit the potassium ion current in an in vitro voltage-clamp model using isolated whole cells expressing the hERG cardiac potassium channel. The voltage-clamp assay is an accepted pre-clinical method of assessing the potential for pharmaceutical agents to change the pattern of cardiac repolarization, specifically to cause, so-called QT prolongation, which has been associated with cardiac arrhythmia. (Cavero et al., *Opinion on Pharmacotherapy*, 2000, 1, 947-73, Fermini et al., *Nature Reviews Drug Discovery*, 2003, 2, 439-447) Accordingly, pharmaceutical compositions comprising compounds of the invention are expected to be free of such cardiac side effects.

There properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

Boc=tert-butoxycarbonyl
(Boc)$_2$O=di-tert-butyl dicarbonate
DCM=dichloromethane
DMF=N,N-dimethylformamide
DMSO=dimethyl sulfoxide
EtOAc=ethyl acetate
mCPBA=m-chlorobenzoic acid
MeCN=acetonitrile
MTBE=tert-butyl methyl ether
PyBop=benzotriazol-1-yloxytripyrrolidino-phosphonium hexafluorophosphate
R$_f$=retention factor
RT=room temperature
TFA=trifluoroacetic acid
THF=tetrahydrofuran Reagents (including secondary amines) and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC: a general protocol is described below. Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (300 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1100 LC/MSD instrument.

General Protocol for Analytical HPLC

Crude compounds were dissolved in 50% MeCN/H$_2$O (with 0.1% TFA) at 0.5-1.0 mg/mL concentration, and analyzed using the following conditions:

Column: Zorbax Bonus-RP (3.5 μm of particle size, 2.1×50 mm)
Flow rate: 0.5 mL/min
Detector wavelength: 214, 254, and 280 nm.

General Protocol for Preparative HPLC Purification

Crude compounds were dissolved in 50% acetic acid in water at 50-100 mg/mL concentration, filtered, and fractionated using the following procedure:

Column: YMC Pack-Pro C18 (50a×20 mm; ID=5 μm)
Flow rate: 40 mL/min
Mobile Phases: A=90% MeCN/10% H$_2$O/0.1% TFA
B=98% H$_2$O/2% MeCN/0.1% TFA
Gradient: 10% A/90% B to 50% A/50% B over 30 min (linear)
Detector wavelength: 214 nm.

Preparation of Secondary Amines

Thiomorpholine-1,1-dioxide was prepared from thiomorpholine by protection of the secondary amine to N-Boc thiomorpholine ((Boc)$_2$O, MeOH), oxidation to sulfone (mCPBA, CH$_2$Cl$_2$, 0° C.), and deprotection of the N-Boc group to provide the free amine (CF$_3$CO$_2$H, CH$_2$Cl$_2$). (m/z): [M+H]$^+$ calcd for C$_4$H$_9$NO$_2$S, 136.04; found, 135.9.

The N-sulfonyl derivatives of piperazine were prepared from N-Boc piperazine by reacting with respective sulfonyl chloride (iPr$_2$NEt, CH$_2$Cl$_2$, 0° C.), and deprotecting the N-Boc group (CF$_3$CO$_2$H, CH$_2$Cl$_2$). 1-Methanesulfonyl-piperazine: $^1$H-NMR (CDCl$_3$; neutral): δ (ppm) 3.1 (t, 4H), 2.9 (t, 4H), 2.7 (s, 3H). 1-(Methylsulfonyl)methanesulfonyl-piperazine: $^1$H-NMR (CD$_3$OD): δ (ppm) 2.90 (s, 3H), 3.02 (m, 4H), 3.38 (m, 4H), 4.61 (s, 2H).

The racemic or single chiral isomer forms of 3-acetylaminopyrrolidine were prepared by treating N$^1$-Boc-3-aminopyrrolidine (racemate, 3R, or 3S) with acetyl chloride (iPr$_2$NEt, CH$_2$Cl$_2$, 0° C.), and deprotecting the N-Boc group (CF$_3$CO$_2$H, CH$_2$Cl$_2$). 3-(Acetamido)pyrrolidine: $^1$H-NMR (DMSO-d$_6$; TFA salt): δ (ppm) 4.2 (quin, 1H), 3.3-3.1 (m, 3H), 2.9 (m, 1H), 2.0 (m, 1H), 1.8 (br s, 4H).

3-((R)-2-Hydroxypropionamido)pyrrolidine was prepared after amidation of N$^1$-Boc-3-aminopyrrolidine (L-lactic acid, PyBOP, DMF, RT), and deprotection of N-Boc group (CF$_3$CO$_2$H, CH$_2$Cl$_2$). (m/z): [M+H]$^+$ calcd for C$_7$H$_{14}$N$_2$O$_2$, 159.11; found, 159.0. $^1$H-NMR (CD$_3$OD; TFA salt): δ (ppm) 4.4 (quin, 1H), 4.1 (q, 1H), 3.5-3.4 (m, 2H), 3.3-3.2 (m, 2H), 2.3 (m, 1H), 2.0 (m, 1H), 1.3 (d, 3H).

The N$^3$-alkanesulfonyl derivatives of (3R)-aminopyrrolidine were obtained by treating N$^1$-Boc-(3R)-aminopyrrolidine with propionylsulfonyl chloride or cyclohexylmethylsulfonyl chloride (i-Pr$_2$NEt, CH$_2$Cl$_2$, 0° C.), and deprotecting N-Boc group (CF$_3$CO$_2$H, CH$_2$Cl$_2$).

3-(N-Acetyl-N-methylamido)piperidine was prepared from N$^3$-Cbz protected 3-amino-piperidine-1-carboxylic acid t-butyl ester (De Costa, B., et al. *J. Med. Chem.* 1992, 35, 4334-43) after four synthetic steps: i) MeI, n-BuLi, THF, −78° c. to rt; ii) H$_2$ (1 atm), 10% Pd/C, EtOH; iii) AcCl, i-Pr$_2$NEt, CH$_2$Cl$_2$; iv) CF$_3$CO$_2$H, CH$_2$Cl$_2$. m/z: [M+H]$^+$ calcd for C$_8$H$_{16}$N$_2$O: 157.13; found, 157.2. $^1$H-NMR (CD$_3$OD; TFA salt): δ (ppm) 4.6 (m, 1H), 3.3 (m, 1H), 3.2 (m, 1H), 3.0 (m, 1H), 2.9 (s, 3H), 2.8 (m, 1H), 2.0 (s, 3H), 1.9-1.7 (m, 4H).

3-(N-Acetyl-amido)piperidine was prepared from 3-amino-piperidine-1-carboxylic acid tert-butyl ester after N-acetylation and deprotection of the N-Boc group: i) AcCl, i-Pr$_2$NEt, CH$_2$Cl$_2$; ii) CF$_3$CO$_2$H, CH$_2$Cl$_2$. $^1$H-NMR (CD$_3$OD; TFA salt): δ (ppm) 3.9 (m, 1H), 3.3 (dd, 1H), 3.2 (m, 1H), 2.9 (dt, 1H), 2.75 (dt, 1H), 2.0-1.9 (m, 2H), 1.9 (s, 3H), 1.8-1.4 (m, 2H).

The N$^3$-alkanesulfonyl derivatives of 3-aminopiperidine were synthesized by reacting the chiral or racemic forms of 3-amino-piperidine-1-carboxylic acid tert-butyl ester with the respective alkanesulfonyl chloride (i-Pr$_2$NEt, CH$_2$Cl$_2$) and deprotecting the N-Boc group (CF$_3$CO$_2$H, CH$_2$Cl$_2$). (3S)-3-(ethanesulfonylamido)piperidine: $^1$H-NMR (CD$_3$OD): δ (ppm) 1.29 (t, 3H, J$_1$=7.4 Hz), 1.50-1.80 (m, 2H), 1.90-2.10 (m, 2H), 2.89 (m, 2H), 3.05 (q, 2H, J$_1$=7.4 Hz), 3.27 (m, 2H), 3.40 (d of d(br), 1H), 3.52 (m, 1H). 3S-Methylsulfonylmethanesulfonylamido-piperidine: $^1$H-NMR (CD$_3$OD): δ (ppm) 2.13-2.30 (m, 2H), 2.40-2.57 (m, 2H), 2.98 (m, 2H), 3.15 (s, 3H), 3.21 (m, 2H), 3.30 (br d, 1H), 3.74 (m, 1H).

3-(Methylamino)-1-acetylpyrrolidine was prepared from 3-(methylamino)-1-benzylpyrrolidine (TCI America) after four steps: i) (Boc)$_2$O, MeOH, rt; ii) H$_2$ (1 atm), 10% Pd/C, EtOH; iii) AcCl, i-Pr$_2$NEt, CH$_2$Cl$_2$; iv) CF$_3$CO$_2$H, CH$_2$Cl$_2$. (m/z): [M+H]$^+$ calcd for C$_7$H$_{14}$N$_2$O: 143.12; found, 143.0.

3-(Methylamino)-1-(methanesulfonyl)pyrrolidine was prepared from 3-(methylamino)-1-benzylpyrrolidine after four steps: i) (Boc)$_2$O, MeOH, rt; ii) H$_2$ (1 atm), 10% Pd/C, EtOH; iii) CH$_3$SO$_2$Cl, i-Pr$_2$NEt, CH$_2$Cl$_2$; iv) CF$_3$CO$_2$H, CH$_2$Cl$_2$. (m/z): [M+H]$^+$ calcd for C$_6$H$_{14}$N$_2$O$_2$S: 179.08; found, 179.2. 3R-Methylamino-1-(methanesulfonyl)pyrrolidine was prepared in a similar manner from (3R)-(methylamino)-1-benzylpyrrolidine.

Derivatives of tetrahydro-3-thiophenamine-1,1-dioxide were prepared following the protocol of Loev, B. *J. Org. Chem.* 1961, 26, 4394-9 by reacting 3-sulfolene with a requisite primary amine in methanol (cat. KOH, rt). N-Methyl-3-tetrahydrothiopheneamine-1,1-dioxide (TFA salt): $^1$H-NMR (DMSO-d$_6$): δ (ppm) 9.4 (br s, 2H), 4.0-3.8 (quin, 1H), 3.6-3.5 (dd, 1H), 3.4-3.3 (m, 1H), 3.2-3.1 (m, 2H), 2.5 (s, 3H), 2.4 (m, 1H), 2.1 (m, 1H). N-2-(1-hydroxy)ethyl-3-tetrahydrothiopheneamine-1,1-dioxide: (m/z): [M+H]$^+$ calcd for C$_6$H$_{13}$NO$_3$S: 180.07; found, 180.2.

N-Methyl-tetrahydro-2H-thiopyran-4-amine-1,1-dioxide was prepared from tetrahydro-4H-thiopyran-4-one: i) MeNH$_2$, NaBH$_4$; ii) (Boc)$_2$O, MeOH; iii) mCPBA, CH$_2$Cl$_2$, 0° C.; iv) CF$_3$CO$_2$H, CH$_2$Cl$_2$. (m/z): [M+H]$^+$ calcd for C$_6$H$_{13}$NO$_2$S 164.07; found, 164.9. $^1$H-NMR (CD$_3$OD; TFA salt): δ (ppm) 3.4-3.1 (m, 5H), 2.7 (s, 3H), 2.4 (br d, 2H), 2.1 (br m, 2H).

1-Acetyl-3-(methylamino)piperidine was prepared from N$^3$-Cbz protected 3-methylamino-piperidine: i) AcCl, i-Pr$_2$NEt, CH$_2$Cl$_2$; ii) H$_2$ (1 atm), 10% Pd/C, EtOH. $^1$H-NMR (CD$_3$OD): δ (ppm) 4.0 (m, 1H), 3.6 (m, 1H), 3.4-3.2 (m, 2H), 3.0 (m, 1H), 2.6 (s, 3H), 2.1 (s, 3H), 1.8-1.6 (m, 4H).

1-(Methanesulfonyl)-3-(methylamino)piperidine was prepared from N$^3$-Cbz protected 3-methylamino-piperidine: i) CH$_3$SO$_2$Cl, i-Pr$_2$NEt, CH$_2$Cl$_2$; ii) H$_2$ (1 atm), 10% Pd/C, EtOH. (m/z): [M+H]$^+$ calcd for C$_7$H$_{16}$N$_2$O$_2$S 193.10; found, 193.0. $^1$H-NMR (DMSO-d$_6$; TFA salt): δ (ppm) 3.4 (dd, 1H), 3.2 (m, 2H), 3.10 (s, 3H), 3.0-2.9 (m, 2H), 2.8 (s, 3H), 1.85-1.75 (m, 2H), 1.6-1.4 (m, 2H).

Example 1

Synthesis of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide a. Preparation of 8-benzyl-8-azabicyclo[3.2.1]octan-3-one

Concentrated hydrochloric acid (30 mL) was added to a heterogeneous solution of 2,5-dimethoxy tetrahydrofuran (82.2 g, 0.622 mol) in water (170 mL) while stirring. In a separate flask cooled to 0° C. (ice bath), concentrated hydrochloric acid (92 mL) was added slowly to a solution of benzyl amine (100 g, 0.933 mol) in water (350 mL). The 2,5-dimethoxytetrahydrofuran solution was stirred for approximately 20 min, diluted with water (250 mL), and then the benzyl amine solution was added, followed by the addition of a solution of 1,3-acetonedicarboxylic acid (100 g, 0.684 mol) in water (400 mL) and then the addition of sodium hydrogen phosphate (44 g, 0.31 mol) in water (200 mL). The pH was adjusted from pH 1 to pH ~4.5 using 40% NaOH. The resulting cloudy and pale yellow solution was stirred overnight. The solution was then acidified to pH 3 from pH 7.5 using 50% hydrochloric acid, heated to 85° C. and stirred for 2 hours. The solution was cooled to room temperature, basified to pH 12 using 40% NaOH, and extracted with dichloromethane (3×500 mL). The combined organic layers were washed with brine, dried ($MgSO_4$), filtered and concentrated under reduced pressure to produce the crude title intermediate as a viscous brown oil (52 g).

To a solution of the crude intermediate in methanol (1000 mL) was added di-tert-butyl dicarbonate (74.6 g, 0.342 mol) at 0° C. The solution was allowed to warm to room temperature and stirred overnight. The methanol was removed under reduced pressure and the resulting oil was dissolved in dichloromethane (1000 mL). The intermediate was extracted into 1 M $H_3PO_4$ (1000 mL) and washed with dichloromethane (3×250 mL) The aqueous layer was basified to pH 12 using aqueous NaOH, and extracted with dichloromethane (3×500 mL). The combined organic layers were dried ($MgSO_4$), filtered and concentrated under reduced pressure to produce the title intermediate as a viscous, light brown oil (54 g). $^1$H-NMR ($CDCl_3$) δ (ppm) 7.5-7.2 (m, 5H, $C_6H_5$), 3.7 (s, 2H, $CH_2Ph$), 3.45 (broad s, 2H, CH—NBn), 2.7-2.6 (dd, 2H, $CH_2CO$), 2.2-2.1 (dd, 2H, $CH_2CO$), 2.1-2.0 (m, 2H, $CH_2CH_2$), 1.6 (m, 2H, $CH_2CH_2$). (m/z): $[M+H]^+$ calcd for $C_{14}H_{17}NO$ 216.14; found, 216.0.

b. Preparation of 3-oxo-8-azabicyclo[3.2.1]octane-8-carboxylic acid tert-butyl ester To a solution of 8-benzyl-8-azabicyclo[3.2.1]octan-3-one (75 g, 0.348 mol) in EtOAc (300 mL) was added a solution of di-tert-butyl dicarbonate (83.6 g, 0.383 mol, 1.1 eq) in EtOAc (300 mL). The resulting solution and rinse (100 mL EtOAc) was added to a 1 L Parr hydrogenation vessel containing 23 g of palladium hydroxide (20 wt. % Pd, dry basis, on carbon, ~50% wet with water; e.g. Pearlman's catalyst) under a stream of nitrogen. The reaction vessel was degassed (alternating vacuum and $N_2$ five times) and pressurized to 60 psi of $H_2$ gas. The reaction solution was agitated for two days and recharged with $H_2$ as needed to keep the $H_2$ pressure at 60 psi until the reaction was complete as monitored by silica thin layer chromatography. The black solution was then filtered through a pad of Celite® and concentrated under reduced pressure to yield the title intermediate quantitatively as a viscous, yellow to orange oil (51 g). It was used in the next step without further treatment. $^1$H NMR ($CDCl_3$) δ(ppm) 4.5 (broad, 2H, CH—NBoc), 2.7 (broad, 2H, $CH_2CO$), 2.4-2.3 (dd, 2H, $CH_2CH_2$), 2.1 (broad m, 2H, $CH_2CO$), 1.7-1.6 (dd, 2H, $CH_2CH_2$), 1.5 (s, 9H, $(CH_3)_3COCON$)).

c. Preparation of (1S,3R,5R)-3-amino-8-azabicyclo[3.2.1]octane-8-carboxylic acid tert-butyl ester To a solution of the product of the previous step (75.4 g, 0.335 mol) in methanol (1 L) was added ammonium formate (422.5 g, 6.7 mol), water (115 mL) and 65 g of palladium on activated carbon (10% on dry basis, ~50% wet with water; Degussa type E101NE/W) under a stream of $N_2$ while stirring via mechanical stirrer. After 24 and 48 hours, additional portions of ammonium formate (132 g, 2.1 mol) were added each time. Once reaction progression ceased, as monitored by anal. HPLC, Celite® (>500 g) was added and the resulting thick suspension was filtered and then the collected solid was rinsed with methanol (~500 mL). The filtrates were combined and concentrated under reduced pressure until all methanol had been removed. The resulting cloudy, biphasic solution was then diluted with 1M phosphoric acid to a final volume of ~1.5 to 2.0 L at pH 2 and washed with dichloromethane (3×700 mL). The aqueous layer was basified to pH 12 using 40% aq. NaOH, and extracted with dichloromethane (3×700 mL). The combined organic layers were dried over $MgSO_4$, filtered, and concentrated by rotary evaporation, then high-vacuum leaving 52 g (70%) of the title intermediate, commonly N-Boc-endo-3-aminotropane, as a white to pale yellow solid. The isomer ratio of endo to exo amine of the product was >99 based on $^1$H-NMR analysis (>96% purity by analytical HPLC). $^1$H NMR ($CDCl_3$) δ (ppm) 4.2-4.0 (broad d, 2H, CHNBoc), 3.25 (t, 1H, $CHNH_2$), 2.1-2.05 (m, 4H), 1.9 (m, 2H), 1.4 (s, 9H, $(CH_3)_3OCON$), 1.2-1.1 (broad, 2H). (m/z): $[M+H]^+$ calcd for $C_{12}H_{22}N_2O_2$ 227.18; found, 227.2. Analytical HPLC (isocratic method; 2:98 (A:B) to 90:10 (A:B) over 5 min): retention time=2.14 min.

d. Preparation of 1-isopropyl-1H-indazole-3-carboxylic acid

To indazole-3-carboxylic acid (40 g, 247 mmol) suspended in methanol (700 mL) was added concentrated $H_2SO_4$ (10 mL) slowly while stirring the mixture. The mixture was stirred and refluxed at 80° C. for 24 h. The mixture was cooled, filtered, and concentrated under reduced pressure to afford a pale yellow solid. The solid was suspended in water (700 mL), crushed to fine powder, collected by filtration, and rinsed with water (~400 mL). The product was suspended in toluene, and evaporated to dryness under reduced pressure, affording indazole-3-carboxylic acid methyl ester as a pale yellow solid (45 g, >95% pure). (m/z): $[M+H]^+$ calcd for $C_9H_8N_2O_2$ 177.07; found, 177.0. $^1$H-NMR ($CD_3OD$, 300 MHz): δ (ppm) 8.0 (1H, d), 7.5 (1H, d), 7.4 (1H, t), 7.2 (1H, t), 3.9 (3H, s).

To a solution of indazole-3-carboxylic acid methyl ester (40.7 g, 231 mmol) in anhydrous tetrahydrofuran (700 mL) cooled in an ice bath was added slowly solid potassium tert-butoxide (28.3 g, 252 mmol). The mixture was stirred at the same temperature for 1 hr prior to the addition of 2-iodo-dopropane (34.4 mL, 367 mmol). The final mixture was stirred for 12 h at ambient temperature, and refluxed for 12 h. After cooling to room temperature, the mixture was filtered, and the collected solid was rinsed with tetrahydrofuran (100 mL). The filtrates were combined, and concentrated to dryness under reduced pressure, affording crude 1-isopropyl-1H-indazole-3-carboxylic acid methyl ester (49.7 g) as a pale yellow oil. The crude material was purified by flash silica gel chromatography eluting with hexane/ethyl acetate (9/1 to 3/1) to yield 1-isopropyl-1H-indazole-3-carboxylic acid methyl ester (43 g, 197 mmol, >99% pure). $^1$H-NMR (CD$_3$OD, 300 MHz): δ (ppm) 8.1-8.0 (1H, d), 7.6 (1H, d), 7.4 (1H, t), 7.2 (1H, t), 5.0 (1H, quin), 3.9 (s, 3H), 1.5 (6H, d).

To a solution of the methyl ester dissolved in tetrahydrofuran (400 mL) was added 1M NaOH (400 mL). The mixture was stirred for 24 h at ambient temperature. The reaction was terminated by washing with ethyl acetate (2×400 mL), saving the aqueous layer. The aqueous layer was acidified slowly by adding conc. HCl (~40 mL) in an ice bath, which led to separation of a pale yellow oily product. The product was extracted with ethyl acetate (1000 mL), and the organic layer was dried over MgSO$_4$ and evaporated under reduced pressure to yield the title intermediate as a pale yellow to white solid (34 g, >98% pure), which was further purified by crystallization from ethyl acetate to provide the title intermediate as colorless needles. (m/z): [M+Na]$^+$ calcd for C$_{11}$H$_{12}$N$_2$O$_2$ 226.07; found, 226.6. $^1$H-NMR (CD$_3$OD, 300 MHz):): δ (ppm) 8.1-8.0 (1H, d), 7.6 (1H, d), 7.4 (1H, t), 7.2 (1H, t), 5.0 (1H, quin), 1.5 (6H, d).

e. Preparation of (1S,3R,5R)-3-[1-isopropyl-1H-indazole-3-carbonyl)amino]-8-azabicyclo[3.2.1]octane-8-carboxylic acid tert-butyl ester A suspension of 1-isopropyl-1H-indazole-3-carboxylic acid (56.35 g; 0.276 mol) in toluene (500 mL) was stirred and heated for 5 min prior to the addition of thionyl chloride (30.2 mL; 0.414 mol). After heating at 100° C. for 15 min, the mixture became a homogeneous solution, which continued to be stirred at the same temperature for an additional 90 min. In a separate reaction flask, (1S,3R,5R)-3-amino-8-azabicyclo[3.2.1]octane-8-carboxylic acid tert-butyl ester, prepared as in step c, (62.43 g; 0.276 mol) was dissolved in 250 mL of toluene and followed by addition of NaOH (66.3 g) dissolved in 250 mL of water. This biphasic mixture was cooled in an ice bath. The solution of indazole acid chloride prepared above was cooled to room temperature, and added over 15 min to the biphasic solution, which was stirred vigorously in an ice bath. After stirring for 1.5 h, the reaction mixture was transferred to a separatory funnel. First, the aqueous layer was separated from toluene layer (saved), and extracted with EtOAc (2×500 mL). The toluene layer was concentrated under reduced pressure, and the obtained residue was dissolved in the organic extract (1 L; EtOAc). The solution was washed with 1 M H$_3$PO$_4$ (400 mL), sat. NaHCO$_3$ (400 mL), and then brine solution (400 mL). After drying over MgSO$_4$, the organic solution was evaporated to dryness under reduced pressure, yielding 119.2 g of the title intermediate. $^1$H-NMR (DMSO-d$_6$): δ (ppm) 1.41 (s, 9H), 1.51 (d, 6H), 1.82 (m, 2H), 1.97 (bs, 4H), 2.09 (m, 2H), 4.10 (m, 3H), 5.10 (sept, 1H), 7.23 (t, 1H), 7.42 (t, 1H), 7.79 (d, 1H), 7.82 (d, 1H), 8.18 (d, 1H). (m/z): [M+H]$^+$ calcd for C$_{23}$H$_{32}$N$_4$O$_3$, 413.26; found, 413.1. Retention time (anal. HPLC: 2-95% MeCN/H$_2$O over 6 min)=4.85 min.

f. Preparation of 1-isopropyl-1H-indazole-3-carboxylic acid {(1S,3R,5R)-8-aza-bicyclo[3.2.1]oct-3-yl}amide The product for the previous step was solubilized in dichloromethane (200 mL), cooled in an ice bath, and then mixed with 200 mL of trifluoroacetic acid. The reaction mixture was stirred for 1 h at ambient temperature. It was then added dropwise to ethyl ether (2 L) in a flask while being stirred, which afforded the title intermediate as its mono(trifluoroacetic acid) salt (102.7 g after drying, 87% yield over two steps). $^1$H-NMR (DMSO-d$_6$): δ (ppm) 1.54 (d, 6H), 2.05 (m, 2H), 2.24 (m, 6H), 4.03 (s, 2H), 4.12 (q, 1H), 5.09 (sept, 1H), 7.28 (t, 1H), 7.45 (t, 1H), 7.81 (d, 1H), 8.00 (d, 1H), 8.11 (d, 1H), 8.54 (bd, 2H). (m/z): [M+H]$^+$ calcd for C$_{18}$H$_{24}$N$_4$O, 313.20; found, 313.1. Retention time (anal. HPLC: 2-95% MeCN/H$_2$O over 6 min)=2.65 min.

g. Preparation of 1-isopropyl-1H-indazole-3-carboxylic acid {(1S,3R,5R)-8-(2,2-dimethoxyethyl)-8-aza-bicyclo[3.2.1]oct-3-yl}amide To a solution of 1-isopropyl-1H-indazole-3-carboxylic acid {(1S,3R,5R)-8-aza-bicyclo[3.2.1]oct-3-yl}amide (52.7 g; 0.124 mol) dissolved in 500 mL of dichloromethane was added diisopropylethylamine (43.1 mL) and dimethoxy acetaldehyde in tert-butyl methyl ether (cone 45%; 44.5 mL, 0.173 mmol). After stirring 35 min at ambient temperature, sodium triacetoxyborohydride (36.7 g; 0.173 mol) was added to this mixture. The reaction was quenched after 90 min by adding slowly water (50 mL) and sat. NaHCO$_3$ solution (100 mL) in an ice bath. The mixture was diluted with 500 mL of dichloromethane, and transferred to a separatory funnel. The organic layer was collected, and washed with sat. NaHCO$_3$ (250 mL), and brine solution (350 mL). It was dried over MgSO$_4$, and evaporated under reduced pressure, yielding the title intermediate (58.8 g). $^1$H-NMR (CDCl$_3$): δ (ppm) 1.60 (d, 6H), 1.77 (m, 2H), 1.96-2.09 (m, 4H), 2.29 (m, 2H), 2.55 (m, 2H), 3.33 (m, 2H), 3.41 (s, 6H), 4.33 (q, 1H), 4.47 (m, 1H), 4.87 (sept, 1H), 7.26 (t, 1H), 7.37-7.46 (m, 2H), 7.56 (d, 1H), 8.36 (d, 1H). (m/z): [M+H]$^+$ calcd for C$_{22}$H$_{32}$N$_4$O$_3$ 401.26; found, 401.3. Retention time (anal. HPLC: 2-50% MeCN/H$_2$O over 6 min)=4.20 min.

h. Preparation of 1-isopropyl-1H-indazole-3-carboxylic acid {(1S,3R,5R)-8-(2,2-dihydroxyethyl)-8-aza-bicyclo[3.2.1]oct-3-yl}amide The product of the previous step (55.2 g) was suspended in 500 mL of 6 M hydrochloric acid and heated at 70° C. for 1 h. The reaction mixture was cooled to 0° C., and diluted with dichloromethane (500 mL) prior to basification of the aqueous layer by slow addition of 6M NaOH (800 mL). It was further mixed with 800 mL of dichloromethane, and transferred to a separatory funnel. The organic layer was collected, washed with brine, dried over MgSO$_4$, and evaporated to dryness affording the title intermediate (45.1 g). (m/z): [M+H]$^+$ calcd for C$_{20}$H$_{28}$N$_4$O$_3$, 373.22; found, 373.2. Retention time (anal. HPLC: 2-50% MeCN/H$_2$O over 6 min)=3.77 min.

i. Synthesis 1-isopropyl-1H-indazole-3-carboxylic acid {(1S,3R,5R)-8-[2-(4-acetyl-piperazin-1-yl)ethyl]-8-aza-bicyclo[3.2.1]oct-3-yl}amide, alternatively, N-[(3-endo)-8-[2-(4-acetylpiperazin-1-yl)ethyl]-8-azabicyclo[3.2.1]oct-3-yl]-141-methylethyl)-1H-indazole-3-carboxamide To a flask containing 450 mL of dichloromethane was added 1-acetylpiperazine (19.3 g; 0.151 mol), sodium triacetoxyborohydride (34.4 g). It was stirred for 5 min prior to addition of the product of the previous step (45.1 g). The final mixture was stirred for 1 h, at which time the reaction was complete based on HPLC and mass spectrometric analysis.

Water (200 mL) was added slowly and the mixture was diluted with 600 mL of dichloromethane, and shaken in a funnel before collecting the organic layer. It was washed with 1M NaOH (400 mL) and brine (500 mL). Drying over MgSO$_4$, and evaporation afforded the title compound as a colorless solid (47.6 g). The crude product was purified by crystallization from ethanol as the HCl salt (>30 g; purity>98%). $^1$H-NMR (DMSO-d$_6$; free base): δ (ppm) 1.52 (d, 6H), 1.69 (m, 2H), 1.83 (m, 2H), 1.97 (s, 3H), 1.92-2.10 (m, 4H), 2.33 (t, 2H), 2.42 (m, 6H), 2.50 (m, 2H), 3.21 (bs, 2H), 3.38 (m, 4H), 4.09 (q, 1H), 5.07 (sept, 1H), 7.26 (t, 1H), 7.43 (t, 1H), 7.79 (d, 1H), 8.12 (d, 1H). (m/z): [M+H]$^+$ calcd for C$_{26}$H$_{38}$N$_6$O$_2$, 467.31; found, 467.5. Retention time (anal. HPLC: 2-50% MeCN/H$_2$O over 6 min)=3.52 min.

Example 2

Synthesis of 1-isopropyl-1H-indazole-3-carboxylic acid {(1S,3R,5R)-8-[2-(4-(tetrahydrofuran-2-carbonyl)piperazin-1-yl)ethyl]-8-azabicyclo[3.2.1]oct-3-yl}amide To a solution of N-[2-tetrahydrofuroyl]piperazine hydrobromide (40 mg, 0.15 mmol) and N,N-diisopropylethylamine (12 µL, 0.3 mmol) in dichloromethane (1.5 mL) was added sodium triacetoxyborohydride (64 mg, 0.3 mmol), and then 1-isopropyl-1H-indazole-3-carboxylic acid {(1S,3R,5R)-8-(2,2-dihydroxyethyl)-8-aza-bicyclo[3.2.1]oct-3-yl}amide (HCl salt) (39 mg, 0.1 mmol). The mixture was shaken at ambient temperature for 15 min. After concentration under reduced pressure, the reaction mixture was dissolved in 50% aqueous acetic acid, and purified by preparative HPLC to provide the trifluoroacetic acid salt of the title compound (97% purity). (m/z): [M+H]$^+$ calcd for C$_{29}$H$_{42}$N$_6$O$_3$, 523.34; found 523.2. Retention time (anal. HPLC: 5-65% MeCN/H$_2$O over 5 min)=2.7 min.

Examples 3-20

Using processes similar to that of Example 2, except replacing the N-[2-tetrahydrofuroyl]piperazine hydrobromide with the appropriate secondary amine, the compounds of Examples 3-20 were prepared.

Example 3 1-isopropyl-1H-indazole-3-carboxylic acid {(1S,3R,5R)-8-[2-(1,1-dioxo-1λ$^6$-thiomorpholin-4-yl)ethyl]-8-azabicyclo[3.2.1]oct-3-yl}amide; (m/z): [M+H]$^+$ calcd for C$_{24}$H$_{35}$N$_5$O$_3$S, 474.25; found 474.2. Retention time (anal. HPLC: 5-75% MeCN/H$_2$O over 5 min)=2.20 min.

Example 4 1-isopropyl-1H-indazole-3-carboxylic acid {(1S,3R,5R)-8-[2-(4-methanesulfonylpiperazin-1-yl)ethyl]-8-azabicyclo[3.2.1]oct-3-yl}amide; (m/z): [M+H]$^+$ calcd for C$_{25}$H$_{38}$N$_6$O$_3$S, 503.28; found 503.2. Retention time (anal. HPLC: 5-65% MeCN/H$_2$O over 4 min)=2.12 min.

Example 5 1-isopropyl-1H-indazole-3-carboxylic acid {(1S,3R,5R)-8-[2-(4-cyclohexylmethanesulfonylpiperazin-1-yl)ethyl]-8-azabicyclo[3.2.1]oct-3-yl}amide; (m/z): [M+H]$^+$ calcd for C$_{31}$H$_{48}$N$_6$O$_3$S, 585.35; found 585.4. Retention time (anal. HPLC: 5-75% MeCN/H$_2$O over 5 min)=2.67 min.

Example 6 1-isopropyl-1H-indazole-3-carboxylic acid {(1S,3R,5R)-8-[2-(4-methanesulfonylmethanesulfonylpiperazin-1-yl)ethyl]-8-azabicyclo[3.2.1]oct-3-yl}amide; (m/z): [M+H]$^+$ calcd for C$_{26}$H$_{40}$N$_6$O$_5$S$_2$, 581.26; found 581.2. Retention time (anal. HPLC: 5-75% MeCN/H$_2$O over 5 min)=2.22 min.

Example 7 1-isopropyl-1H-indazole-3-carboxylic acid {(1S,3R,5R)-8-[2-(3-(acetyl-methylamino)pyrrolidin-1-yl)ethyl]-8-azabicyclo[3.2.1]oct-3-yl}amide; (m/z): [M+H]$^+$ calcd for C$_{27}$H$_{40}$N$_6$O$_2$, 481.32; found 481.3. Retention time (anal. HPLC: 5-75% MeCN/H$_2$O over 5 min)=2.07 min.

Example 8 1-isopropyl-1H-indazole-3-carboxylic acid {(1S,3R,5R)-8-[2-(3-(acetyl-amino)pyrrolidin-1-yl)ethyl]-8-azabicyclo[3.2.1]oct-3-yl}amide; (m/z): [M+H]$^+$ calcd for C$_{26}$H$_{38}$N$_6$O$_2$, 467.31; found 467.4. Retention time (anal. HPLC: 5-75% MeCN/H$_2$O over 5 min)=1.89 min.

Example 9 1-isopropyl-1H-indazole-3-carboxylic acid {(1S,3R,5R)-8-[2-((R)-3-(acetyl-amino)pyrrolidin-1-yl)ethyl]-8-azabicyclo[3.2.1]oct-3-yl}amide; (m/z): [M+H]$^+$ calcd for C$_{26}$H$_{38}$N$_6$O$_2$, 467.31; found 467.4. Retention time (anal. HPLC: 5-75% MeCN/H$_2$O over 5 min)=2.04 min.

Example 10 1-isopropyl-1H-indazole-3-carboxylic acid {(1S,3R,5R)-8-[2-(S)-3-(acetyl-amino)pyrrolidin-1-yl)ethyl]-8-azabicyclo[3.2.1]oct-3-yl}amide; (m/z): [M+H]$^+$ calcd for C$_{26}$H$_{38}$N$_6$O$_2$, 467.31; found 467.4. Retention time (anal. HPLC: 5-75% MeCN/H$_2$O over 5 min)=2.07 min.

Example 11 1-isopropyl-1H-indazole-3-carboxylic acid ((1S,3R,5R)-8-{2-[3-((S)-2-hydroxypropionylamino)pyrrolidin-1-yl]ethyl}-8-azabicyclo[3.2.1]oct-3-yl)amide; (m/z): [M+H]$^+$ calcd for C$_{27}$H$_{40}$N$_6$O$_3$, 497.32; found 497.2. Retention time (anal. HPLC: 5-65% MeCN/H$_2$O over 5 min)=2.07 min.

Example 12 1-isopropyl-1H-indazole-3-carboxylic acid ((1S,3R,5R)-8-{2-[(3S,4S)-3-(acetylmethylamino)-4-hydroxypyrrolidin-1-yl]ethyl}-8-azabicyclo[3.2.1]oct-3-yl)amide; (m/z): [M+H]$^+$ calcd for C$_{27}$H$_{40}$N$_6$O$_3$, 497.32; found 497.2. Retention time (anal. HPLC: 5-65% MeCN/H$_2$O over 5 min)=2.15 min.

Example 13 1-isopropyl-1H-indazole-3-carboxylic acid {(1S,3R,5R)-8-[2-((R)-3-ethanesulfonylaminopyrrolidin-1-yl)ethyl]-8-azabicyclo[3.2.1]oct-3-yl}amide; (m/z): [M+H]$^+$ calcd for C$_{26}$H$_{40}$N$_6$O$_3$S, 517.30; found 517.2. Retention time (anal. HPLC: 5-75% MeCN/H$_2$O over 5 min)=2.12 min.

Example 14 1-isopropyl-1H-indazole-3-carboxylic acid {(1S,3R,5R)-8-[2-((R)-3-cyclohexylmethanesulfonylaminopyrrolidin-1-yl)ethyl]-8-azabicyclo[3.2.1]oct-3-yl}amide; (m/z): [M+H]$^+$ calcd for C$_{31}$H$_{48}$N$_6$O$_3$S, 585.36; found 585.4. Retention time (anal. HPLC: 5-75% MeCN/H$_2$O over 5 min)=2.52 min.

Example 15 1-isopropyl-1H-indazole-3-carboxylic acid ((1S,3R,5R)-8-{2-[3-(acetyl-methylamino)piperidin-1-yl]ethyl}-8-azabicyclo[3.2.1]oct-3-yl)amide; (m/z): [M+H]$^+$ calcd for C$_{28}$H$_{42}$N$_6$O$_2$, 495.34; found 495.4. Retention time (anal. HPLC: 5-75% MeCN/H$_2$O over 5 min)=1.94 min.

Example 16 1-isopropyl-1H-indazole-3-carboxylic acid {(1S,3R,5R)-8-[2-(3-acetylaminopiperidin-1-yl)ethyl]-8-azabicyclo[3.2.1]oct-3-yl}amide; (m/z): [M+H]$^+$ calcd for C$_{27}$H$_{40}$N$_6$O$_2$, 481.33; found 481.2. Retention time (anal. HPLC: 5-75% MeCN/H$_2$O over 5 min)=2.01 min.

Example 17 1-isopropyl-1H-indazole-3-carboxylic acid {(1S,3R,5R)-8-[2-(3-methanesulfonylaminopiperidin-1-yl)ethyl]-8-azabicyclo[3.2.1]oct-3-yl}amide; (m/z): [M+H]$^+$ calcd for C$_{26}$H$_{40}$N$_6$O$_3$S, 517.30; found 517.4. Retention time (anal. HPLC: 5-75% MeCN/H$_2$O over 5 min)=1.97 min.

Example 18 1-isopropyl-1H-indazole-3-carboxylic acid {(1S,3R,5R)-8-[2-((S)-3-methanesulfonylaminopiperidin-1-yl)ethyl]-8-azabicyclo[3.2.1]oct-3-yl}amide; (m/z): [M+H]$^+$ calcd for C$_{26}$H$_{40}$N$_6$O$_3$S, 517.30; found 517.4. Retention time (anal. HPLC: 5-75% MeCN/H$_2$O over 5 min)=1.99 min.

Example 19 1-isopropyl-1H-indazole-3-carboxylic acid {(1S,3R,5R)-8-[2-((S)-3-ethanesulfonylaminopiperidin-1-yl)ethyl]-8-azabicyclo[3.2.1]oct-3-yl}amide; (m/z): [M+H]$^+$ calcd for $C_{27}H_{42}N_6O_3S$, 531.31; found 531.4. Retention time (anal. HPLC: 5-75% MeCN/H$_2$O over 5 min)=2.04 min.

Example 20 1-isopropyl-1H-indazole-3-carboxylic acid {(1S,3R,5R)-8-[2-((S)-3-methanesulfonylmethanesulfonylaminopiperidin-1-yl)ethyl]-8-azabicyclo[3.2.1]oct-3-yl}amide; (m/z): [M+H]$^+$ calcd for $C_{27}H_{42}N_6O_5S_2$, 595.27; found 595.2. Retention time (anal. HPLC: 5-75% MeCN/H$_2$O over 5 min)=2.07 min.

Example 21

Synthesis of 1-isopropyl-1H-indazole-3-carboxylic acid ((1S,3R,5R)-8-{2-[(1-acetylpyrrolidin-3-yl)methylamino]ethyl}-8-azabicyclo[3.2.1]oct-3-yl)amide To a solution of 3-(methylamino)-1-acetylpyrrolidine (43 mg, 0.3 mmol) and N,N-diisopropylethylamine (12 µL, 0.3 mmol) in dichloromethane (1.5 mL) was added sodium triacetoxyborohydride (128 mg, 0.6 mmol), and then 1-isopropyl-1H-indazole-3-carboxylic acid {(1S,3R,5R)-8-(2,2-dihydroxyethyl)-8-aza-bicyclo[3.2.1]oct-3-yl}amide (HCl salt) (78 mg, 0.2 mmol). The mixture was shaken at ambient temperature for 15 min. After concentration under reduced pressure, the reaction mixture was dissolved in 50% aqueous acetic acid, and purified by preparative HPLC to provide the trifluoroacetic acid salt of the title compound (56 mg, 99% purity). (m/z): [M+H]$^+$ calcd for $C_{27}H_{40}N_6O_2$, 481.33; found 481.2. Retention time (anal. HPLC: 5-65% MeCN/H$_2$O over 5 min)=2.00 min.

Examples 22-30

Using processes similar to that of Example 21, except replacing the 3-(methylamino)-1-acetylpyrrolidine with the appropriate secondary amine, the compounds of Examples 22-30 were prepared.

Example 22 1-isopropyl-1H-indazole-3-carboxylic acid ((1S,3R,5R)-8-{2-[((R)-1-acetylpyrrolidin-3-yl)methylamino]ethyl}-8-azabicyclo[3.2.1]oct-3-yl)amide; (m/z): [M+H]$^+$ calcd for $C_{27}H_{40}N_6O_2$, 481.33; found 481.4. Retention time (anal. HPLC: 10-50% MeCN/H$_2$O over 5 min)=2.52 min.

Example 23 1-isopropyl-1H-indazole-3-carboxylic acid ((1S,3R,5R)-8-{2-[((S)-1-acetylpyrrolidin-3-yl)methylamino]ethyl}-8-azabicyclo[3.2.1]oct-3-yl)amide; (m/z): [M+H]$^+$ calcd for $C_{27}H_{40}N_6O_2$, 481.33; found 481.4. Retention time (anal. HPLC: 10-50% MeCN/H$_2$O over 5 min)=2.52 min.

Example 24 1-isopropyl-1H-indazole-3-carboxylic acid ((1S,3R,5R)-8-{2-[(1-methanesulfonylpyrrolidin-3-yl)methylamino]ethyl}-8-azabicyclo[3.2.1]oct-3-yl)amide; (m/z): [M+H]$^+$ calcd for $C_{26}H_{40}N_6O_3S$, 517.30; found 517.2. Retention time (anal. HPLC: 5-75% MeCN/H$_2$O over 5 min)=2.04 min.

Example 25 1-isopropyl-1H-indazole-3-carboxylic acid ((1S,3R,5R)-8-{2-[((R)-1-methanesulfonylpyrrolidin-3-yl)methylamino]ethyl}-8-azabicyclo[3.2.1]oct-3-yl)amide; (m/z): [M+H]$^+$ calcd for $C_{26}H_{40}N_6O_3S$, 517.30; found 517.2. Retention time (anal. HPLC: 5-65% MeCN/H$_2$O over 5 min)=2.20 min.

Example 26 1-isopropyl-1H-indazole-3-carboxylic acid ((1S,3R,5R)-8-{2-[(1,1-dioxo-tetrahydro-1λ$^6$-thiophen-3-yl)methylamino]ethyl}-8-azabicyclo[3.2.1]oct-3-yl)amide; (m/z): [M+H]$^+$ calcd for $C_{25}H_{37}N_5O_3S$, 488.27; found 488.2. Retention time (anal. HPLC: 5-75% MeCN/H$_2$O over 5 min)=2.22 min.

Example 27 1-isopropyl-1H-indazole-3-carboxylic acid ((1S,3R,5R)-8-{2-[(1,1-dioxo-tetrahydro-1λ$^6$-thiophen-3-yl)-(2-hydroxyethyl)amino]ethyl}-8-azabicyclo[3.2.1]oct-3-yl)amide; (m/z): [M+H]$^+$ calcd for $C_{26}H_{39}N_5O_4S$, 518.28; found 518.2. Retention time (anal. HPLC: 5-65% MeCN/H$_2$O over 5 min)=2.25 min.

Example 28 1-isopropyl-1H-indazole-3-carboxylic acid ((1S,3R,5R)-8-{2-[(1-acetyl-piperidin-3-yl)methylamino]ethyl}-8-azabicyclo[3.2.1]oct-3-yl)amide; (m/z): [M+H]$^+$ calcd for $C_{26}H_{38}N_6O_2$, 495.34; found 495.4. Retention time (anal. HPLC: 5-75% MeCN/H$_2$O over 5 min)=1.95 min.

Example 29 1-isopropyl-1H-indazole-3-carboxylic acid ((1S,3R,5R)-8-{2-[(1,1-dioxo-hexahydro-1λ$^6$-thiopyran-4-yl)methylamino]ethyl}-8-azabicyclo[3.2.1]oct-3-yl)amide; (m/z): [M+H]$^+$ calcd for $C_{26}H_{39}N_5O_3S$, 502.29 found 502.2. Retention time (anal. HPLC: 5-65% MeCN/H$_2$O over 5 min)=2.12 min.

Example 30 1-isopropyl-1H-indazole-3-carboxylic acid ((1S,3R,5R)-8-{2-[(1-methanesulfonylpiperidin-3-yl)methylamino]ethyl}-8-azabicyclo[3.2.1]oct-3-yl)amide; (m/z): [M+H]$^+$ calcd for $C_{27}H_{42}N_6O_3S$, 531.31; found 531.4. Retention time (anal. HPLC: 5-75% MeCN/H$_2$O over 5 min)=2.07 min.

Example 31

Synthesis of 5-fluoro-1-isopropyl-1H-indazole-3-carboxylic acid {(1S,3R,5R)-8-[2-(4-acetylpiperazin-1-yl)ethyl]-8-azabicyclo[3.2.1]oct-3-yl}amide a. Preparation of 5-fluoro-1-isopropyl-1H-indazole-3-carboxylic acid 5-Fluoro-1H-indazole-3-carboxylic acid methyl ester was prepared according to the protocol described in (Buu-Hoi, N. P., et al. *J. Hetereocyclic Chem.* 1964, 1, 239-41. $^1$H-NMR (DMSO-d$_6$): δ (ppm) 7.8 (dd, 2H), 7.35 (dt, 1H), 3.8 (s, 3H). The methyl ester was alkylated at N$^1$ with isopropyl iodide in the presence of potassium tert-butoxide in refluxing THF. $^1$H-NMR (CDCl$_3$): δ (ppm) 7.8 (dd, 1H), 7.6 (dd, 1H), 7.1 (dt, 1H), 4.8 (hept, 1H), 1.6 (d, 6H). The isopropyl methyl ester was then hydrolyzed (1 M NaOH/THF, RT) to provide the title intermediate.

b. Preparation of 5-fluoro-1-isopropyl-1H-indazole-3-carboxylic acid {(1S,3R,5R)-8-aza-bicyclo[3.2.1]oct-3-yl}amide The title intermediate was prepared according to the procedure of Example 1 parts e and f, using the intermediate of the previous step in place of 1-isopropyl-1H-indazole-3-carboxylic acid. $^1$H-NMR (DMSO-d$_6$): δ (ppm) 7.9 (br, 1H), 7.7 (dd, 1H), 7.6 (dd, 1H), 7.2 (dt, 1H), 4.9 (m, 1H), 4.2 (br, 1H), 4.0 (br, 2H), 2.3-2.1 (br m, 8H), 1.5 (d, 6H). (m/z): [M+H]$^+$ calcd for $C_{18}H_{23}FN_4O$, 331.19; found, 331.4. Retention time (anal. HPLC: 10-40% MeCN/H$_2$O over 6 min)=3.43 min.

c. Preparation of 5-fluoro-1-isopropyl-1H-indazole-3-carboxylic acid {(1S,3R,5R)-8-(2,2-dimethoxyethyl)-8-aza-bicyclo[3.2.1]oct-3-yl}amide The product of the previous step was reacted with dimethoxy acetaldehyde according to the process of Example 1 step g to provide the title intermediate. (m/z): [M+H]+ calcd for $C_{22}H_{31}FN_4O_3$ 419.25; found, 419.3.

d. Preparation of 5-fluoro-1-isopropyl-1H-indazole-3-carboxylic acid {(1S,3R,5R)-8-(2,2-dihydroxy-ethyl)-8-aza-bicyclo[3.2.1]oct-3-yl}amide The intermediate of the previous step (1.0 g) was suspended in 10 mL of 6 M hydrochloric acid and heated at 70° C. for 1 h. The reaction mixture was cooled, and evaporated under reduced pressure to dryness to afford the hydrochloric acid salt of the title intermediate. (m/z): [M+H]+ calcd for $C_{20}H_{27}FN_4O_3$, 391.21; found, 391.4.

e. Synthesis of 5-fluoro-1-isopropyl-1H-indazole-3-carboxylic acid {(1S,3R,5R)-8-[2-(4-acetylpiperazin-1-yl)ethyl]-8-azabicyclo[3.2.1]oct-3-yl}amide To a flask containing 40 mL of dichloromethane was added 1-acetylpiperazine (613 mg; 4.78 mmol) and sodium triacetoxyborohydride (1.01 g). It was stirred for 5 min prior to addition of the product of the previous step (~1 g). The final mixture was stirred for 1 h, at which the reaction was complete based on HPLC and mass spectrometric analysis. Water (20 mL) was added slowly and the mixture was diluted with 300 mL of dichloromethane, and shaken in a funnel before collecting the organic layer. It was washed with 1M NaOH (100 mL) and brine (100 mL). Drying over $MgSO_4$, and evaporation afforded the title compound which was purified by preparative HPLC to afford 380 mg of pure product as the TFA salt. $^1$H-NMR (DMSO-$d_6$; free base): δ (ppm) 8.0 (br, 1H), 7.8 (dd, 1H), 7.6 (dd, 1H), 7.23 (dt, 1H), 5.0 (hept, 1H), 4.0-3.9 (br, 3H), 3.5 (br, 2H), 3.2-2.8 (br, 10H), 2.2 (br m, 8H), 1.9 (s, 3H), 1.4 (d, 6H). (m/z): [M+H]+ calcd for $C_{26}H_{37}FN_6O_2$, 485.30; found, 485.5. Retention time (anal. HPLC: 10-70% MeCN/$H_2O$ over 6 min)=2.28 min.

Example 32

Synthesis of 1-propyl-1H-indazole-3-carboxylic acid {(1S,3R,5R)-8-[2-(4-acetylpiperazin-1-yl)ethyl]-8-azabicyclo[3.2.1]oct-3-yl}amide a. Preparation of 1H-indazole-3-carboxylic acid {(1S,3R,5R)-8-[2-(4-acetylpiperazin-1-yl)ethyl]-8-azabicyclo[3.2.1]oct-3-yl}amide The title intermediate was prepared according to the procedure of Example 1 using 1H-indazole-3-carboxylic acid in place of 1-isopropyl-1H-indazole-3-carboxylic acid in step e. (m/z): [M+H]+ calcd for $C_{23}H_{32}N_6O_2$, 425.27; found, 425.4. Retention time (anal. HPLC: 10-40% MeCN/$H_2O$ over 6 min)=1.47 min.

b. Alternative synthesis of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide To a solution of anhydrous DMF (2 mL) containing the TFA salt of the intermediate of the previous step (80 mg, 0.123 mmol) was added potassium tert-butoxide (48 mg, 0.43 mmol) and isopropyl iodide (37 μL, 0.368 mmol). The mixture was shaken at 85° C. for 12 h, and then evaporated to dryness, affording pale brown residue, which was dissolved in 50% aq. acetic acid, and fractionated by preparative HPLC to afford the title compound. (m/z): calcd for $C_{26}H_{38}N_6O_2$, 467.31; obsd. 467.2 [M+H]+. Retention time (anal. HPLC: 5-65% MeCN/$H_2O$ over 6 min)=2.09 min.

c. Synthesis of 1-propyl-1H-indazole-3-carboxylic acid {(1S,3R,5R)-8-[2-(4-acetylpiperazin-1-yl)ethyl]-8-azabicyclo[3.2.1]oct-3-yl}amide Using a process similar to that of step b, except replacing the isopropyl iodide with n-propyl iodide, the title compound was prepared. (m/z): [M+H]+ calcd for $C_{26}H_{38}N_6O_2$, calcd. 467.31; obsd. 467.4 [M+H]+. Retention time (anal. HPLC: 5-65% MeCN/$H_2O$ over 6 min)=2.05 min.

Examples 33-35

Using processes similar to that of Example 32, except replacing the isopropyl iodide with the appropriate alkyl halide, the compounds of Examples 33-35 were prepared.

Example 33 1-butyl-1H-indazole-3-carboxylic acid ((1S,3R,5R)-8-[2-(4-acetylpiperazin-1-yl)ethyl]-8-azabicyclo[3.2.1]oct-3-yl}amide; (m/z): [M+H]+ calcd for $C_{27}H_{40}N_6O_2$, 481.33; found 481.4. Retention time (anal. HPLC: 5-65% MeCN/$H_2O$ over 6 min)=216 min.

Example 34 1-cyclobutyl-1H-indazole-3-carboxylic acid ((1S,3R,5R)-8-[2-(4-acetylpiperazin-1-yl)ethyl]-8-azabicyclo[3.2.1]oct-3-yl}amide; (m/z): [M+H]+ calcd for $C_{27}H_{38}N_6O_2$, 479.31; found 479.4. Retention time (anal. HPLC: 5-65% MeCN/$H_2O$ over 6 min)=2.20 min.

Example 35 1-cyclopentyl-1H-indazole-3-carboxylic acid ((1S,3R,5R)-8-[2-(4-acetylpiperazin-1-yl)ethyl]-8-azabicyclo[3.2.1]oct-3-yl}amide; (m/z): [M+H]+ calcd for $C_{28}H_{40}N_6O_2$, 493.33; found 493.2. Retention time (anal. HPLC: 5-65% MeCN/$H_2O$ over 6 min)=2.34 min.

Examples 36-40

Using processes similar to those described above, the compounds of Examples 36-40 can be prepared.

Example 36 1-isopropyl-1H-indazole-3-carboxylic acid {(1S,3R,5R)-8-[2-((R)-3-(acetyl-methylamino)pyrrolidin-1-yl)ethyl]-8-azabicyclo[3.2.1]oct-3-yl}amide.

Example 37 1-isopropyl-1H-indazole-3-carboxylic acid {(1S,3R,5R)-8-[2-((S)-3-(acetyl-methylamino)pyrrolidin-1-yl)ethyl]-8-azabicyclo[3.2.1]oct-3-yl}amide.

Example 38 1-isopropyl-1H-indazole-3-carboxylic acid ((1S,3R,5R)-8-{2-[((S)-1-methanesulfonylpyrrolidin-3-yl)methylamino]ethyl}-8-azabicyclo[3.2.1]oct-3-yl)amide.

Example 39 1-isopropyl-1H-indazole-3-carboxylic acid ((1S,3R,5R)-8-{2-[(R)-(1,1-dioxo-tetrahydro-1$\lambda^6$-thiophen-3-yl)methylamino]ethyl}-8-azabicyclo[3.2.1]oct-3-yl)amide.

Example 40 1-isopropyl-1H-indazole-3-carboxylic acid ((1S,3R,5R)-8-{2-[(S)-(1,1-dioxo-tetrahydro-1$\lambda^6$-thiophen-3-yl)methylamino]ethyl}-8-azabicyclo[3.2.1]oct-3-yl)amide.

Example 41

Synthesis of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide dihydrochloride a. Preparation of (1S,3R,5R)-3-[1-isopropyl-1H-indazole-3-carbonyl)amino]-8-azabicyclo[3.2.1]octane-8-carboxylic acid tert-butyl ester A 5 L three-necked round bottom flask equipped with a magnetic stir bar, a reflux condenser, an addition funnel, a nitrogen inlet and a thermometer was charged with 1-isopropyl-1H-indazole-3-carboxylic acid (250 g, 1.224 mol, 1.1 eq) and 2.5 L of toluene. The resulting suspension was stirred and heated at 70-80° C. To this suspension was added thionyl chloride (218.4 g, 1.836 mol, 1.65 eq) over a period of 40 min. The mixture was heated at 90-100° C. for 1 h and was cooled to 25° C.

A separate 12 L three-necked round bottom flask equipped with a mechanical stirrer, an addition funnel, a nitrogen inlet and a thermometer was charged with 2.5 L of toluene and 3 N NaOH (prepared from diluting 356 g of 50% NaOH with water to 1.48 L), and (1S,3R,5R)-3-amino-8-azabicyclo[3.2.1]octane-8-carboxylic acid tert-butyl ester (251.9 g, 1.113 mol, 1 eq). The resulting suspension was stirred at 23° C. for 10 min and was cooled to 5° C. To this suspension was added the acid chloride solution in toluene over a period of 90 min keeping the internal temperature at ~5° C. throughout the addition period. The mixture was stirred for 30 min. The reaction was warmed to 25° C.; the aqueous layer was discarded (1.58 L, pH>13). The organic layer was washed with 1 L of 20 wt % brine; and the aqueous layer was discarded (1.005 L, ~pH 8). The organic layer was collected (5.3 L) and was concentrated to half of the volume (~2.6 L), and was used in the following step without purification b. Preparation of 1-isopropyl-1H-indazole-3-carboxylic acid {(1S,3R,5R)-8-aza-bicyclo[3.2.1]oct-3-yl}amide A 12 L three-necked round bottom flask equipped with a mechanical stirrer, an addition funnel, a nitrogen inlet and a thermometer was charged with the product of the previous step. To this solution was added trifluoroacetic acid (0.65 L) over a period of 10 min. The resulting mixture was stirred for 1 h at ambient temperature.

Water (3.3 L) was added to the reaction mixture. The resulting suspension was stirred at 23° C. for 10 min and was allowed to settle to give a three-layer mixture. The top two layers were discarded and the bottom layer (820 mL) was collected and added to MTBE (6560 mL) over a period of 90 min. The resulting suspension was cooled to 5° C. and was agitated for 1 h. The suspension was filtered; the wet cake was washed with MTBE (500 mL), and dried under reduced pressure (80 mm Hg) for 60 h to give the title intermediate (386 g, 81% yield, 99.2% purity by HPLC) as an off-white sandy solid.

c. Preparation of 1-isopropyl-1H-indazole-3-carboxylic acid {(1S,3R,5R)-8-(2,2-dimethoxyethyl)-8-aza-bicyclo[3.2.1]oct-3-yl}amide A 3 L three-necked round bottom flask equipped with a magnetic stirrer, a nitrogen inlet and a thermometer was charged with the intermediate of the previous step (84 g, 0.197 mol), dichloromethane (840 mL), and sodium triacetoxyborohydride (62.6 g, 0.295 mol). The resulting suspension was stirred for 10 min, cooled to 10° C. and 60 wt % aqueous dimethoxyacetaldehyde (51.3 g, 0.295 mol) was added. This solution was stirred for 30 min, warmed to 25° C., and stirred for 1 h. The mixture was filtered through Celite, washed with dichloromethane (150 mL) and then with 5 wt % brine solution (400 g). The aqueous and organic layers were separated and the organic layer was concentrated to a dark oil (~150 mL), which was used in the following step without purification.

d. Preparation of 1-isopropyl-1H-indazole-3-carboxylic acid {(1S,3R,5R)-8-(2,2-dihydroxyethyl)-8-aza-bicyclo[3.2.1]oct-3-yl}amide A 1 L three-necked round bottom flask equipped with a magnetic stirrer, a nitrogen inlet and a thermometer was charged with the product of the previous step and water (250 mL) and heated to 50-55° C. To this solution was added 3N HCl (82 mL, 0.985 mol). The resulting mixture was stirred at 75° C. for 1 h. The reaction mixture was cooled to 25° C. and neutralized with 25 wt % NaOH (159 g, 0.99 mol) to pH 3.51. After about 20 min, the lower layer was collected (~120 mL) to provide the title intermediate, which was used in the following step without purification.

e. Synthesis of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide dihydrochloride A 3 L three-necked round bottom flask equipped with a magnetic stirrer, a nitrogen inlet and a thermometer was charged with sodium triacetoxyborohydride (84 g, 0.349 mol) and dichloromethane (800 mL). The resulting mixture was stirred at 25° C. and charged with 1-acetylpiperazine (51 g, 0.394 mol). The addition assembly was rinsed with dichloromethane (20 mL). The mixture was stirred for 5 min and charged with the product of the previous step (~120 mL) in 15 min maintaining the internal temperature less than 25° C. The mixture was stirred for 15 min, filtered through Celite and washed with dichloromethane (2×100 mL). The filtrate was washed with 1N NaOH (500 mL). The layers were separated and the lower organic layer was collected and concentrated to ~150 mL.

Absolute ethanol (250 mL) was added and the mixture was concentrated to ~200 mL. To this mixture, absolute ethanol (800 mL) was added and the mixture was heated to 40° C. To this mixture, 3 N HCl (33 mL, 0.396 mol) was added in 3 min. The mixture was stirred for 10 min and crystallization began. The resulting suspension was stirred at 55° C. for 2 h and cooled to 25° C. The mixture was filtered though Whatman #2 filter paper and the wet cake was washed with absolute ethanol (2×100 mL). The product was dried under nitrogen for 30 min and then under vacuum at 40-50° C. for 24 h to provide the title compound (82 g).

Example 42

Synthesis of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide dihydrobromide A 500 mL three-necked round bottom flask equipped with a magnetic stirrer, a nitrogen inlet and a thermometer was charged with water (120 mL) and 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide dihydrochloride (12 g, 22.2 mmol). The resulting mixture was stirred to give a light yellow clear solution. To this solution was added 25 wt % NaOH (7.83 g, 24.4 mmol) in 2 min to give a white milky suspension. Dichloromethane (120 mL) was added and the mixture was stirred for 30 min to give a clear two-layer solution. The layers were separated to give an aqueous layer (113 mL) and an organic layer (125 mL), which was washed with 10% aqueous NaBr (120 mL). The layers were separated to give an organic layer (120 mL) which was concentrated to about one-quarter volume. Absolute ethanol (250 mL) was added and the mixture was distilled to give ~200 mL total volume. The solution was stirred at 58° C. and 48 wt % aqueous HBr (8.2 g, 49 mmol) was added in 2 min. Precipitation was observed when more than half of the HBr was added. The mixture was stirred at 55° C. to 62° C. for 1 h and then cooled to ambient temperature and filtered. The filtrate was washed with absolute ethanol (40 mL), dried under nitrogen for 20 min and dried at 45° C. under vacuum for 48 h to give the title compound (13.42 g) as a white solid.

Example 43

Synthesis of fumaric acid salt of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide To a solution of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide (0.1 g, 0.21 mmol) in 50% acetonitrile/water (1 mL) was added an ethanolic 1M fumaric acid solution (0.44 mL 0.42 mmol). The resulting solution was lyophilized overnight and then mixed with ethyl acetate (1 mL). Hot ethanol was added to this mixture with heating until a homogeneous solution was obtained (0.4 mL). The resulting clear solution was then allowed to crystallize at room temperature. The resulting solid was filtered, washed with ethanol, and dried under vacuum to give the title compound as a solid (0.13 g).

Example 44

Synthesis of phosphoric acid salt of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide To a solution of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide (0.2 g, 0.43 mmol) in methanol (3 mL) was added an ethanolic 1M phosphoric acid solution (0.43 mL, 0.43 mmol). The resulting heterogeneous solution was then heated to solubilize, filtered, and allowed to cool overnight. The resulting solid was filtered, washed with methanol and dried under vacuum to give the title compound as a solid (0.08 g).

Example 45

Synthesis of p-toluene sulfonic acid salt of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide A solution of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide (38.7 mg, 0.08 mmol) in isopropanol (2 mL) was heated in a 75° C. water bath and solid p-toluenesulfonic acid monohydrate (32.3 mg, 0.17 mmol) was added. The resulting solution was heated until the solids dissolved and then allowed to cool to room temperature. Crystals of the title compound formed overnight.

Example 46

Synthesis of acid salts of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide Using procedures similar to those of Examples 43-45, the following acid salts of 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide were prepared in solid form using the number of equivalents of acid indicated in parentheses: acetate (2); benzoate (2); nitrate (2); propionate (1); tartrate (2); phosphate (0.5).

Example 47

Radioligand Binding Assay on 5-HT$_{4(c)}$ Human Receptors a. Membrane Preparation 5-HT$_{4(c)}$ HEK-293 (human embryonic kidney) cells stably-transfected with human 5-HT$_{4(c)}$ receptor cDNA (Bmax=~6.0 μmol/mg protein, as determined using [$^3$H]-GR113808 membrane radioligand binding assay) were grown in T-225 flasks in Dulbecco's Modified Eagles Medium (DMEM) containing 4,500 mg/L D-glucose and pyridoxine hydrochloride (GIBCO-Invitrogen Corp., Carlsbad Calif.: Cat #11965) supplemented with 10% fetal bovine serum (FBS) (GLBCO-Invitrogen Corp.: Cat #10437), 2 mM L-glutamine and (100 units) penicillin-(100 μg) streptomycin/ml (GIBCO-Invitrogen Corp.: Cat #15140) in a 5% CO$_2$, humidified incubator at 37° C. Cells were grown under continuous selection pressure by the addition of 800 μg/mL geneticin (GIBCO-Invitrogen Corp.: Cat #10131) to the medium.

Cells were grown to roughly 60-80% confluency (<35 subculture passages). At 20-22 hours prior to harvesting, cells were washed twice and fed with serum-free DMEM. All steps of the membrane preparation were performed on ice. The cell monolayer was lifted by gentle mechanical agitation and trituration with a 25 mL pipette. Cells were collected by centrifugation at 1000 rpm (5 min).

For the membrane preparation, cell pellets were resuspended in ice-cold 50 mM 4-(2-hydroxyethyl)-1-piperazineethanesulphonic acid (HEPES), pH 7.4 (membrane preparation buffer) (40 mL/total cell yield from 30-40 T225 flasks) and homogenized using a polytron disrupter (setting 19, 2×10 s) on ice. The resultant homogenates were centrifuged at 1200 g for 5 min at 4° C. The pellet was discarded and the supernatant centrifuged at 40,000 g (20 min). The pellet was washed once by resuspension with membrane preparation buffer and centrifugation at 40,000 g (20 min). The final pellet was resuspended in 50 mM HEPES, pH 7.4 (assay buffer) (equivalent 1 T225 flask/1 mL). Protein concentration of the membrane suspension was determined by the method of Bradford (Bradford, 1976). Membranes were stored frozen in aliquots at −80° C.

b. Radioligand Binding Assays

Radioligand binding assays were performed in 1.1 mL 96-deep well polypropylene assay plates (Axygen) in a total assay volume of 400 μL containing 2 μg membrane protein in 50 mM HEPES pH 7.4, containing 0.025% bovine serum albumin (BSA). Saturation binding studies for determination of IQ values of the radioligand were performed using [$^3$H]-GR113808 (Amersham Inc., Bucks, UK: Cat #TRK944; specific activity ~82 Ci/mmol) at 8-12 different concentrations ranging from 0.001 nM-5.0 nM. Displacement assays for determination of pK$_i$ values of compounds were performed with [³H]-GR113808 at 0.15 nM and eleven different concentrations of compound ranging from 10 pM-100 μM.

Test compounds were received as 10 mM stock solutions in DMSO and diluted to 400 μM into 50 mM HEPES pH 7.4 at 25° C., containing 0.1% BSA, and serial dilutions (1:5) then made in the same buffer. Non-specific binding was determined in the presence of 1 μM unlabeled GR113808. Assays were incubated for 60 min at room temperature, and then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 μL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 1 μM GR113808. $K_i$ values for test compounds were calculated, in Prism, from the best-fit $IC_{50}$ values, and the $K_d$ value of the radioligand, using the Cheng-Prusoff equation (Cheng and Prusoff, *Biochemical Pharmacology*, 1973, 22, 3099-108): $K_i = IC_{50}/(1+[L]/K_d)$ where [L]=concentration [³H]-GR113808. Results are expressed as the negative decadic logarithm of the $K_i$ values, $pK_i$.

Test compounds having a higher $pK_i$ value in this assay have a higher binding affinity for the 5-HT$_4$ receptor. The compounds of the invention which were tested in this assay had a $pK_i$ value ranging from about 6.3 to about 9.0, typically ranging from about 7.0 to about 8.6.

Example 48

Radioligand Binding Assay on 5-HT$_{3A}$ Human Receptors: Determination of Receptor Subtype Selectivity a. Membrane Preparation 5-HT$_{3A}$ HEK-293 (human embryonic kidney) cells stably-transfected with human 5-HT$_{3A}$ receptor cDNA were obtained from Dr. Michael Bruess (University of Bonn, GDR) (Bmax=~9.0 pmol/mg protein, as determined using [³H]-GR65630 membrane radioligand binding assay). Cells were grown in T-225 flasks or cell factories in 50% Dulbecco's Modified Eagles Medium (DMEM) (GIBCO-Invitrogen Corp., Carlsbad, Calif.: Cat #11965) and 50% Ham's F12 (GIBCO-Invitrogen Corp.: Cat #11765) supplemented with 10% heat inactivated fetal bovine serum (FBS) (Hyclone, Logan, Utah: Cat #SH30070.03) and (50 units) penicillin-(50 μg) streptomycin/ml (GIBCO-Invitrogen Corp.: Cat #15140) in a 5% CO$_2$, humidified incubator at 37° C.

Cells were grown to roughly 70-80% confluency (<35 subculture passages). All steps of the membrane preparation were performed on ice. To harvest the cells, the media was aspirated and cells were rinsed with Ca$^{2+}$, Mg$^{2+}$-free Dulbecco's phosphate buffered saline (dPBS). The cell monolayer was lifted by gentle mechanical agitation. Cells were collected by centrifugation at 1000 rpm (5 min). Subsequent steps of the membrane preparation followed the protocol described above for the membranes expressing 5-HT$_{4(c)}$ receptors.

b. Radioligand Binding Assays

Radioligand binding assays were performed in 96-well polypropylene assay plates in a total assay volume of 200 μL containing 1.5-2 μg membrane protein in 50 mM HEPES pH 7.4, containing 0.025% BSA assay buffer. Saturation binding studies for determination of $K_d$ values of the radioligand were performed using [³H]-GR65630 (PerkinElmer Life Sciences Inc., Boston, Mass.: Cat #NET1011, specific activity ~85 Ci/mmol) at twelve different concentrations ranging from 0.005 nM to 20 nM. Displacement assays for determination of $pK_i$ values of compounds were performed with [³H]-GR65630 at 0.50 nM and eleven different concentrations of compound ranging from 10 pM to 100 μM. Compounds were received as 10 mM stock solutions in DMSO (see section 3.1), diluted to 400 μM into 50 mM HEPES pH 7.4 at 25° C., containing 0.1% BSA, and serial (1:5) dilutions then made in the same buffer. Non-specific binding was determined in the presence of 10 μM unlabeled MDL72222. Assays were incubated for 60 min at room temperature, then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 μL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed using the non-linear regression procedure described above to determine $K_i$ values. The BOTTOM (curve minimum) was fixed to the value for non-specific binding, as determined in the presence of 10 μM MDL72222. The quantity [L] in the Cheng-Prusoff equation was defined as the concentration [³H]-GR65630.

Selectivity for the 5-HT$_4$ receptor subtype with respect to the 5-HT$_3$ receptor subtype was calculated as the ratio $K_i(5\text{-}HT_{3A})/K_i(5\text{-}HT_{4(c)})$. The compounds of the invention which were tested in this assay had a 5-HT$_4$/5-HT$_3$ receptor subtype selectivity ranging from about 25 to about 4000, typically ranging from about 100 to about 4000.

Example 49

Whole-cell cAMP Accumulation Flashplate Assay with HEK-293 Cells Expressing Human 5-HT$_{4(c)}$ Receptors In this assay, the functional potency of a test compound was determined by measuring the amount of cyclic AMP produced when HEK-293 cells expressing 5-HT$_4$ receptors were contacted with different concentrations of test compound.

a. Cell Culture

HEK-293 (human embryonic kidney) cells stably-transfected with cloned human 5-HT$_{4(c)}$ receptor cDNA were prepared expressing the receptor at two different densities: (1) at a density of about 0.5-0.6 pmol/mg protein, as determined using a [³H]-GR113808 membrane radioligand binding assay, and (2) at a density of about 6.0 pmol/mg protein. The cells were grown in T-225 flasks in Dulbecco's Modified Eagles Medium (DMEM) containing 4,500 mg/L D-glucose (GIBCO-Invitrogen Corp.: Cat #11965) supplemented with 10% fetal bovine serum (FBS) (GIBCO-Invitrogen Corp.: Cat #10437) and (100 units) penicillin-(100 μg) streptomycin/ml (GIBCO-Invitrogen Corp.: Cat #15140) in a 5% CO$_2$, humidified incubator at 37° C. Cells were grown under continuous selection pressure by the addition of geneticin (800 μg/mL: GIBCO-Invitrogen Corp.: Cat #10131) to the medium.

b. Cell Preparation

Cells were grown to roughly 60-80% confluency. Twenty to twenty-two hours prior to assay, cells were washed twice, and fed, with serum-free DMEM containing 4,500 mg/L D-glucose (GIBCO-Invitrogen Corp.: Cat #11965). To harvest the cells, the media was aspirated and 10 mL Versene (GIBCO-Invitrogen Corp.: Cat #15040) was added to each T-225 flask. Cells were incubated for 5 min at RT and then dislodged from the flask by mechanical agitation. The cell suspension was transferred to a centrifuge tube containing an equal volume of pre-warmed (37° C.) dPBS and centrifuged for 5 min at 1000 rpm. The supernatant was discarded and the pellet was re-suspended in pre-warmed (37° C.) stimulation buffer (10 mL equivalent per 2-3 T-225 flasks). This time was noted and marked as time zero. The cells were counted with a Coulter counter (count above 8 μm, flask yield was $1-2\times10^7$ cells/flask). Cells were resuspended at a concentration of $5\times10^5$ cells/ml in pre-warmed (37° C.) stimulation buffer (as provided in the flashplate kit) and preincubated at 37° C. for 10 min.

cAMP assays were performed in a radioimmunoassay format using the Flashplate Adenylyl Cyclase Activation Assay System with $^{125}$I-cAMP (SMP004B, PerkinElmer Life Sciences Inc., Boston, Mass.), according to the manufacturer's instructions.

Cells were grown and prepared as described above. Final cell concentrations in the assay were $25\times10^3$ cells/well and the final assay volume was 100 μL. Test compounds were received as 10 mM stock solutions in DMSO, diluted to 400 μM into 50 mM HEPES pH 7.4 at 25° C., containing 0.1% BSA, and serial (1:5) dilutions then made in the same buffer. Cyclic AMP accumulation assays were performed with 11 different concentrations of compound ranging from 10 pM to 100 μM (final assay concentrations). A 5-HT concentration-response curve (10 pM to 100 μM) was included on every plate. The cells were incubated, with shaking, at 37° C. for 15 min and the reaction terminated by addition of 100 μl of ice-cold detection buffer (as provided in the flashplate kit) to each well. The plates were sealed and incubated at 4° C. overnight. Bound radioactivity was quantified by scintillation proximity spectroscopy using the Topcount (Packard Bio-Science Co., Meriden, Conn.).

The amount of cAMP produced per mL of reaction was extrapolated from the cAMP standard curve, according to the instructions provided in the manufacturer's user manual. Data were analyzed by nonlinear regression analysis with the GraphPad Prism Software package using the 3-parameter sigmoidal dose-response model (slope constrained to unity). Potency data are reported as $pEC_{50}$ values, the negative decadic logarithm of the $EC_{50}$ value, where $EC_{50}$ is the effective concentration for a 50% maximal response.

Test compounds exhibiting a higher $pEC_{50}$ value in this assay have a higher potency for agonizing the 5-HT$_4$ receptor. The compounds of the invention which were tested in this assay, for example, in the cell line (1) having a density of about 0.5-0.6 pmol/mg protein, had a $pEC_{50}$ value ranging from about 6.3 to about 9.0, typically ranging from about 7.5 to about 8.5.

Example 50

In vitro Voltage Clamp Assay of Inhibition of Potassium Ion Current in Whole Cells Expressing the hERG Cardiac Potassium Channel CHO-K1 cells stably transfected with hERG cDNA were obtained from Gail Robertson at the University of Wisconsin. Cells were held in cryogenic storage until needed. Cells were expanded and passaged in Dulbecco's Modified Eagles Medium/F 12 supplemented with 10% fetal bovine serum and 200 μg/mL geneticin. Cells were seeded onto poly-D-lysine (100 μg/mL) coated glass coverslips, in 35 mm$^2$ dishes (containing 2 mL medium) at a density that enabled isolated cells to be selected for whole cell voltage-clamp studies. The dishes were maintained in a humidified, 5% $CO_2$ environment at 37° C.

Extracellular solution was prepared at least every 7 days and stored at 4° C. when not in use. The extracellular solution contained (mM): NaCl (137), KCl (4), $CaCl_2$ (1.8), $MgCl_2$ (1), Glucose (10), 4-(2-hydroxyethyl)-1-piperazineethane-sulphonic acid (HEPES) (10), pH 7.4 with NaOH. The extracellular solution, in the absence or presence of test compound, was contained in reservoirs, from which it flowed into the recording chamber at approximately 0.5 mL/min. The intracellular solution was prepared, aliquoted and stored at −20° C. until the day of use. The intracellular solution contained (mM): KCl (130), $MgCl_2$ (1), ethylene glycol-bis(beta-aminoethyl ether) N,N,N',N'-tetra acetic acid salt (EGTA) (5), MgATP (5), 4-(2-hydroxyethyl)-1-piperazineethanesulphonic acid (HEPES) (10), pH 7.2 with KOH. All experiments were performed at room temperature (20-22° C.).

The coverslips on which the cells were seeded were transferred to a recording chamber and perfused continuously. Gigaohm seals were formed between the cell and the patch electrode. Once a stable patch was achieved, recording commenced in the voltage clamp mode, with the initial holding potential at −80 mV. After a stable whole-cell current was achieved, the cells were exposed to test compound. The standard voltage protocol was: step from the holding potential of −80 mV to +20 mV for 4.8 sec, repolarize to −50 mV for 5 sec and then return to the original holding potential (−80 mV). This voltage protocol was run once every 15 sec (0.067 Hz). Peak current amplitudes during the repolarization phase were determined using pClamp software. Test compounds at a concentration of 3 μM were perfused over the cells for 5 minutes, followed by a 5-minute washout period in the absence of compound. Finally a positive control (cisapride, 20 nM) was added to the perfusate to test the function of the cell. The step from −80 mV to +20 mV activates the hERG channel, resulting in an outward current. The step back to −50 mV results in an outward tail current, as the channel recovers from inactivation and deactivates.

Peak current amplitudes during the repolarization phase were determined using pCLAMP software. The control and test article data were exported to Origin® (OriginLab Corp., Northampton Mass.) where the individual current amplitudes were normalized to the initial current amplitude in the absence of compound. The normalized current means and standard errors for each condition were calculated and plotted versus the time course of the experiment.

Comparisons were made between the observed $K^+$ current inhibitions after the five-minute exposure to either the test article or vehicle control (usually 0.3% DMSO). Statistical comparisons between experimental groups were performed using a two-population, independent t-test (Microcal Origin v. 6.0). Differences were considered significant at p<0.05.

The smaller the percentage inhibition of the potassium ion current in this assay, the smaller the potential for test compounds to change the pattern of cardiac repolarization when used as therapeutic agents. The compounds of the invention which were tested in this assay at a concentration of 3 μM exhibited an inhibition of the potassium ion current of less than about 20%, typically, less than about 15%.

Example 51

In vitro Model of Oral Bioavailability: Caco-2 Permeation Assay

The Caco-2 permeation assay was performed to model the ability of test compounds to pass through the intestine and get into the blood stream after oral administration. The rate at which test compounds in solution permeate a cell monolayer designed to mimic the tight junction of human small intestinal monolayers was determined.

Caco-2 (colon, adenocarcinoma; human) cells were obtained from ATCC (American Type Culture Collection; Rockville, Md.). For the permeation study, cells were seeded at a density of 63,000 cells/cm$^2$ on pre-wetted transwells polycarbonate filters (Costar; Cambridge, Mass.). A cell monolayer was formed after 21 days in culture. Following cell culture in the transwell plate, the membrane containing the cell monolayer was detached from the transwell plate and inserted into the diffusion chamber (Costar; Cambridge, Mass.). The diffusion chamber was inserted into the heating block which was equipped with circulating external, thermostatically regulated 37° C. water for temperature control. The air manifold delivered 95% $O_2$/5% $CO_2$ to each half of a diffusion chamber and created a laminar flow pattern across the cell monolayer, which was effective in reducing the unstirred boundary layer.

The permeation study was performed with test compound concentrations at 100 µM and with $^{14}$C-mannitol to monitor the integrity of the monolayer. All experiments were conducted at 37° C. for 60 min. Samples were taken at 0, 30 and 60 min from both the donor and receiver sides of the chamber. Samples were analyzed by HPLC or liquid scintillation counting for test compound and mannitol concentrations. The permeation coefficient ($K_P$) in cm/sec was calculated.

In this assay, a $K_p$ value greater than about $10 \times 10^{-6}$ cm/sec is considered indicative of favorable bioavailability. The compounds of the invention that were tested in this assay exhibited $K_p$ values of between about $15 \times 10^{-6}$ cm/sec and about $50 \times 10^{-6}$ cm/sec, typically between about $20 \times 10^{-6}$ cm/sec and about $40 \times 10^{-6}$ cm/sec.

Example 52

Pharmacokinetic Study in the Rat

Aqueous solution formulations of test compounds were prepared in 0.1% lactic acid at a pH of between about 5 and about 6. Male Sprague-Dawley rats (CD strain, Charles River Laboratories, Wilmington, Mass.) were dosed with test compounds via intravenous administration (IV) at a dose of 2.5 mg/kg or by oral gavage (PO) at a dose of 5 mg/kg. The dosing volume was 1 mL/kg for IV and 2 mL/kg for PO administration. Serial blood samples were collected from animals pre-dose, and at 2 (IV only), 5, 15, and 30 min, and at 1, 2, 4, 8, and 24 hours post-dose. Concentrations of test compounds in blood plasma were determined by liquid chromatography-mass spectrometry analysis (LC-MS/MS) (MDS SCIEX, API 4000, Applied Biosystems, Foster City, Calif.) with a lower limit of quantitation of 1 ng/mL.

Standard pharmacokinetic parameters were assessed by non-compartmental analysis (Model 201 for IV and Model 200 for PO) using WinNonlin (Version 4.0.1, Pharsight, Mountain View, Calif.). The maximum in the curve of test compound concentration in blood plasma vs. time is denoted $C_{max}$. The area under the concentration vs. time curve from the time of dosing to the last measurable concentration (AUC (0-t)) was calculated by the linear trapezoidal rule. Oral bioavailability (F(%)), i.e. the dose-normalized ratio of AUC(0-t) for PO administration to AUC(0-t) for IV administration, was calculated as:

$$F(\%) = AUC_{PO}/AUC_{IV} \times Dose_{IV}/Dose_{PO} \times 100\%$$

Test compounds which exhibit larger values of the parameters $C_{max}$, AUC(0-t), and F(%) in this assay are expected to have greater bioavailability when administered orally. The compounds of the invention that were tested in this assay had $C_{max}$ values ranging from about 0.05 to about 0.35 µg/mL, typically ranging from about 0.1 to about 0.35 µg/mL and AUC(0-t) values ranging from about 0.15 to about 0.8 µg·hr/mL, typically ranging from about 0.25 to about 0.8 µg·hr/mL. By way of example, the compound of Example 1 had a $C_{max}$ value of 0.25 µg/mL, an AUC(0-t) value of 0.73 µg·hr/mL and oral bioavailability (F(%)) in the rat model of about 100%.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A method of treating a disorder of reduced motility of the gastrointestinal tract in a mammal, the method comprising administering to the mammal a therapeutically effective amount of a pharmaceutical composition comprising a pharmaceutically-acceptable carrier and a compound of formula (I):

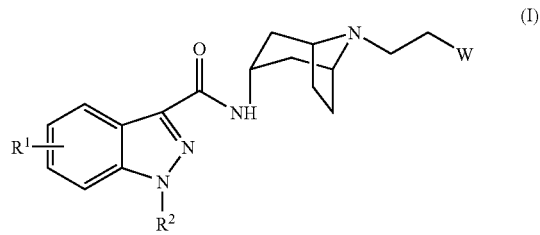

wherein:
R$^1$ is hydrogen, halo, hydroxy, C$_{1-4}$alkyl, or C$_{1-4}$alkoxy;
R$^2$ is C$_{3-4}$alkyl, or C$_{3-6}$cycloalkyl; and
W is selected from:
(i) a group of formula (II):

wherein X is:
NC(O)R$^a$, wherein R$^a$ is C$_{1-3}$alkyl or tetrahydrofuranyl, wherein C$_{1-3}$alkyl is optionally substituted with —OH or C$_{1-3}$alkoxy;
S(O)$_2$; or
NS(O)$_2$R$^b$, wherein R$^b$ is methyl, optionally substituted with —OH, C$_{1-3}$alkoxy, C$_{5-6}$cycloalkyl, or —S(O)$_2$—C$_{1-3}$alkyl;

(ii) a group of formula (III):

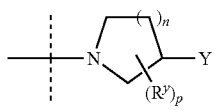

wherein:
R$^y$ is —OH or C$_{1-3}$alkoxy;
p is 0 or 1;
n is 1 or 2; and
Y is:
NR$^c$C(O)R$^d$, wherein R$^c$ is hydrogen or C$_{1-3}$alkyl and R$^d$ is C$_{1-3}$alkyl, optionally substituted with —OH or C$_{1-3}$alkoxy, or
NR$^e$S(O)$_2$R$^f$, wherein R$^e$ is hydrogen and R$^f$ is C$_{1-3}$alkyl, optionally substituted with —OH, C$_{1-3}$alkoxy, C$_{5-6}$cycloalkyl, or —S(O)$_2$—C$_{1-3}$alkyl;
and
(iii) a group of formula (IV):

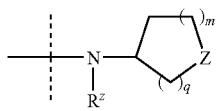

wherein:
R$^z$ is hydrogen, C$_{1-3}$alkyl, or C$_{2-3}$alkyl substituted with —OH or C$_{1-3}$alkoxy;
m is 1 or 2;
q is 1 or 2, provided that the sum of m and q is not equal to 4; and
Z is:
NC(O)R$^g$, wherein R$^g$ is C$_{1-3}$alkyl, optionally substituted with —OH or C$_{1-3}$alkoxy,
S(O)$_2$; or
NS(O)$_2$R$^h$, wherein R$^h$ is methyl, optionally substituted with —OH, C$_{1-3}$alkoxy, C$_{5-6}$cycloalkyl, or —S(O)$_2$—C$_{1-3}$alkyl;
or a pharmaceutically-acceptable salt or stereoisomer thereof.

2. The method of claim 1 wherein R$^1$ is hydrogen or halo and R$^2$ is isopropyl or C$_{4-5}$cycloalkyl.

3. The method of claim 1 wherein W is a group of formula (II) wherein R$^a$ is C$_{1-3}$alkyl and R$^b$ is methyl.

4. The method of claim 1 wherein W is a group of formula (III) wherein p is 0 and n is 1.

5. The method of claim 1 wherein W is a group of formula (IV) wherein m is 1 and q is 1.

6. The method of claim 1:
wherein:
R$^1$ is hydrogen or halo;
R$^2$ is C$_{3-4}$alkyl or C$_{4-5}$cycloalkyl; and
W is selected from the group consisting of:
(i) a group of formula (II) wherein X is NC(O)CH$_3$, S(O)$_2$, or NS(O)$_2$CH$_3$;
(ii) a group of formula (III) wherein p is 0, n is 1, and Y is NCH$_3$C(O)CH$_3$; and
(iii) a group of formula (IV) wherein R$^z$ is methyl, m is 1, q is 1, and Z is NC(O)CH$_3$, S(O)$_2$, or NS(O)$_2$CH$_3$.

7. The method of claim 1 wherein the disorder of reduced motility is chronic constipation, constipation-predominant irritable bowel syndrome, diabetic and idiopathic gastroparesis, or functional dyspepsia.

8. The method of claim 6 wherein the disorder of reduced motility is chronic constipation, constipation-predominant irritable bowel syndrome, diabetic and idiopathic gastroparesis, or functional dyspepsia.

9. A method of treating a mammal having a medical condition ameliorated by treatment with a 5-HT$_4$ receptor agonist, wherein the medical condition is irritable bowel syndrome, chronic constipation, functional dyspepsia, delayed gastric emptying, gastroesophageal reflux disease, gastroparesis, post-operative ileus, intestinal pseudo-obstruction, or drug-induced delayed transit, the method comprising administering to the mammal, a therapeutically effective amount of a pharmaceutical composition comprising a pharmaceutically-acceptable carrier and a compound of formula (I):

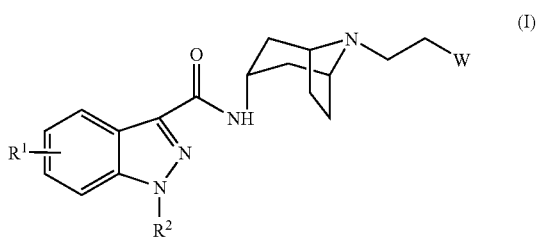

wherein:
R$^1$ is hydrogen, halo, hydroxy, C$_{1-4}$alkyl, or C$_{1-4}$alkoxy;
R$^2$ is C$_{3-4}$alkyl, or C$_{3-6}$cycloalkyl; and
W is selected from:
(i) a group of formula (II):

wherein X is:
NC(O)R$^a$, wherein R$^a$ is C$_{1-3}$alkyl or tetrahydrofuranyl, wherein C$_{1-3}$ alkyl is optionally substituted with —OH or C$_{1-3}$alkoxy;
S(O)$_2$; or
NS(O)$_2$R$^b$, wherein R$^b$ is methyl, optionally substituted with —OH, C$_{1-3}$alkoxy, C$_{5-6}$cycloalkyl, or —S(O)$_2$—C$_{1-3}$alkyl;
(ii) a group of formula (III):

wherein:
R$^y$ is —OH or C$_{1-3}$alkoxy;
p is 0 or 1;
n is 1 or 2; and

Y is:
 NR$^c$C(O)R$^d$, wherein R$^c$ is hydrogen or C$_{1-3}$alkyl and R$^d$ is C$_{1-3}$alkyl optionally substituted with —OH or C$_{1-3}$alkoxy, or
 NR$^e$S(O)$_2$R$^f$, wherein R$^e$ is hydrogen and R$^f$ is C$_{1-3}$alkyl, optionally substituted with —OH, C$_{1-3}$alkoxy, C$_{5-6}$cycloalkyl, or —S(O)$_2$—C$_{1-3}$alkyl;

and (iii) a group of formula (IV):

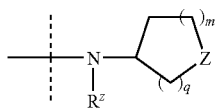

(IV)

wherein:
 R$^z$ is hydrogen, C$_{1-3}$alkyl, or C$_{2-3}$alkyl substituted with —OH or C$_{1-3}$alkoxy;
 m is 1 or 2;
 q is 1 or 2, provided that the sum of m and q is not equal to 4; and Z is:
 NC(O)R$^g$, wherein R$^g$ is C$_{1-3}$alkyl, optionally substituted with —OH or C$_{1-3}$alkoxy,
 S(O)$_2$; or
 NS(O)$_2$R$^h$, wherein R$^h$ is methyl, optionally substituted with —OH, C$_{1-3}$alkoxy, C$_{5-6}$cycloalkyl, or —S(O)$_2$—C$_{1-3}$alkyl;

or a pharmaceutically-acceptable salt or stereoisomer thereof.

10. The method of claim 9 wherein:
 R$^1$ is hydrogen or halo;
 R$^2$ is C$_{3-4}$alkyl or C$_{4-5}$cycloalkyl; and
 W is selected from the group consisting of:
  (i) a group of formula (II) wherein X is NC(O)CH$_3$, S(O)$_2$, or NS(O)$_2$CH$_3$;
  (ii) a group of formula (III) wherein p is 0, n is 1, and Y is NCH$_3$C(O)CH$_3$; and
  (iii) a group of formula (IV) wherein R$^z$ is methyl, m is 1, q is 1, and Z is NC(O)CH$_3$, S(O)$_2$, or NS(O)$_2$CH$_3$.

* * * * *